United States Patent
Oberleitner et al.

[19]

[11] Patent Number: 6,068,815

[45] Date of Patent: May 30, 2000

[54] ENDOSCOPE REPROCESSING AND STERILIZATION SYSTEM

[75] Inventors: Raymond Paul Oberleitner, Zimmerman; John E. Marxer, Eagan; Ward J. Sly, Brooklyn Park; Patricia M. Stanley, Minneapolis; Gregory Worsnick, Chaska; Kurt J. Weimer, Excelsior; Bruce D. Martin; Mary Beth B. Henderson, both of Minneapolis; Bradley K. Onstad, Champlin, all of Minn.

[73] Assignee: Minntech Corporation, Minneapolis, Minn.

[21] Appl. No.: 09/409,663

[22] Filed: Sep. 30, 1999

Related U.S. Application Data

[60] Provisional application No. 60/102,663, Oct. 1, 1998, provisional application No. 60/102,664, Oct. 1, 1998, and provisional application No. 60/117,401, Jan. 27, 1999.

[51] Int. Cl.[7] ................................................... A61L 2/00
[52] U.S. Cl. ........................... 422/28; 422/292; 422/300; 134/170; 134/26; 134/22.12; 134/95.3
[58] Field of Search ..................... 422/292, 300, 422/28; 134/170, 26, 22.12, 95.3

[56] References Cited

U.S. PATENT DOCUMENTS

| | | |
|---|---|---|
| 3,893,843 | 7/1975 | Fry et al. . |
| 4,067,691 | 1/1978 | McGrady et al. . |
| 4,261,950 | 4/1981 | Bainbridge et al. . |
| 4,278,101 | 7/1981 | Tanaka et al. . |
| 4,281,674 | 8/1981 | Tanaka et al. . |
| 4,299,244 | 11/1981 | Hirai . |
| 4,354,514 | 10/1982 | Sundheimer et al. . |
| 4,489,741 | 12/1984 | Ogasawara . |
| 4,517,081 | 5/1985 | Amiot et al. . |
| 4,526,623 | 7/1985 | Ishii et al. . |
| 4,579,597 | 4/1986 | Sasa et al. . |
| 4,644,478 | 2/1987 | Stephens et al. . |
| 4,721,123 | 1/1988 | Cosentino et al. . |
| 4,763,678 | 8/1988 | Ott . |
| 4,892,706 | 1/1990 | Kralovic . |
| 4,943,414 | 7/1990 | Jacobs et al. . |
| 5,217,698 | 6/1993 | Siegel . |
| 5,225,160 | 7/1993 | Sanford . |
| 5,279,799 | 1/1994 | Moser . |
| 5,288,467 | 2/1994 | Biermaier . |
| 5,310,524 | 5/1994 | Campbell . |
| 5,399,314 | 3/1995 | Samuel et al. . |
| 5,425,815 | 6/1995 | Parker et al. . |
| 5,443,801 | 8/1995 | Langford . |
| 5,492,672 | 2/1996 | Childers et al. . |
| 5,494,637 | 2/1996 | Barlow . |
| 5,529,750 | 6/1996 | Kochte . |
| 5,552,115 | 9/1996 | Malchesky . |
| 5,556,607 | 9/1996 | Childers et al. . |
| 5,558,841 | 9/1996 | Nakagawa et al. . |

(List continued on next page.)

FOREIGN PATENT DOCUMENTS

| | | |
|---|---|---|
| 2 248 188 | 4/1992 | United Kingdom . |
| WO 97/17665 | 5/1997 | WIPO . |

OTHER PUBLICATIONS

UNITROL (Infection Control Division of Minntech Corporation); AERO PLUS Automatic Endoscope Reprocessor, 1994 Brochure.

UNITROL (Infection Control Division of Minntech Corporation); AERO Automatic Endoscope Reprocessor, 1994 Brochure.

*Primary Examiner*—Elizabeth H McKane
*Assistant Examiner*—Jennifer McNeil
*Attorney, Agent, or Firm*—Nixon & Vanderhye PC

[57] ABSTRACT

A system for reprocessing and sterilizing a previously used endoscope having at least one lumen is disclosed. The reprocessing system includes a reaction chamber into which individual chemical components of a sterilant are transferred by pneumatic force. The system includes a central processor which controls the asynchronous reprocessing and sterilization of at least two endoscopes. A novel sterilant is also disclosed. Also disclosed is a combination of the sterilization device and the sterilant and methods of using the same.

32 Claims, 13 Drawing Sheets

U.S. PATENT DOCUMENTS

| | | |
|---|---|---|
| 5,711,921 | 1/1998 | Langford . |
| 5,733,503 | 3/1998 | Kowatsch et al. . |
| 5,746,988 | 5/1998 | Hall . |
| 5,753,195 | 5/1998 | Langford et al. . |
| 5,792,435 | 8/1998 | Mueller et al. . |
| 5,795,404 | 8/1998 | Murphy et al. . |
| 5,858,305 | 1/1999 | Malchesky . |

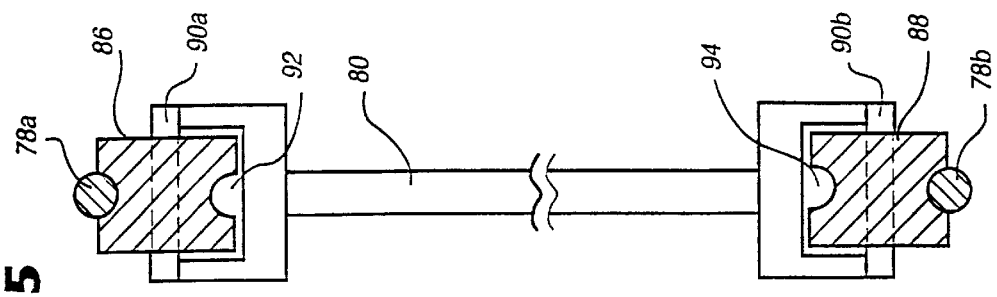
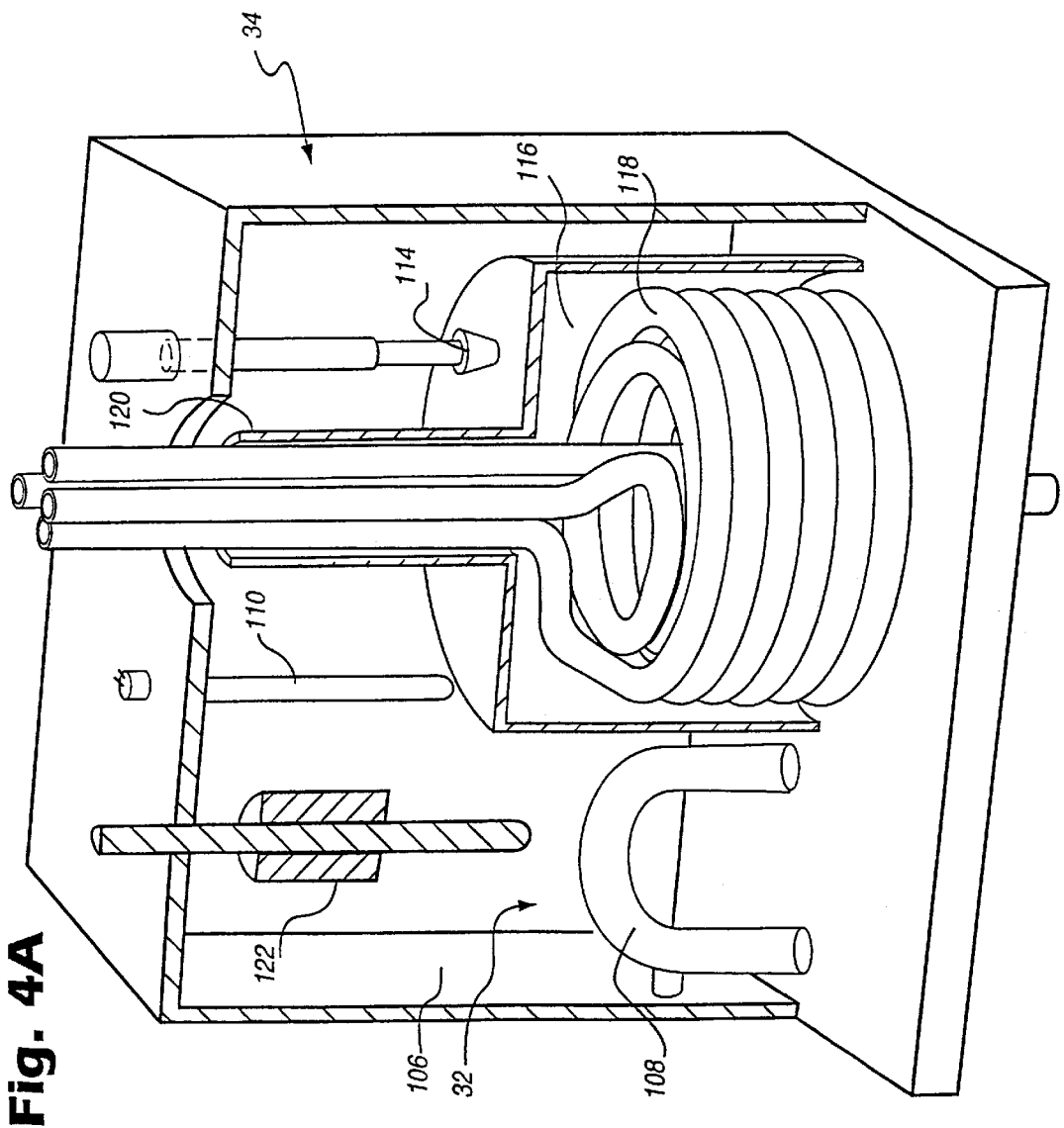

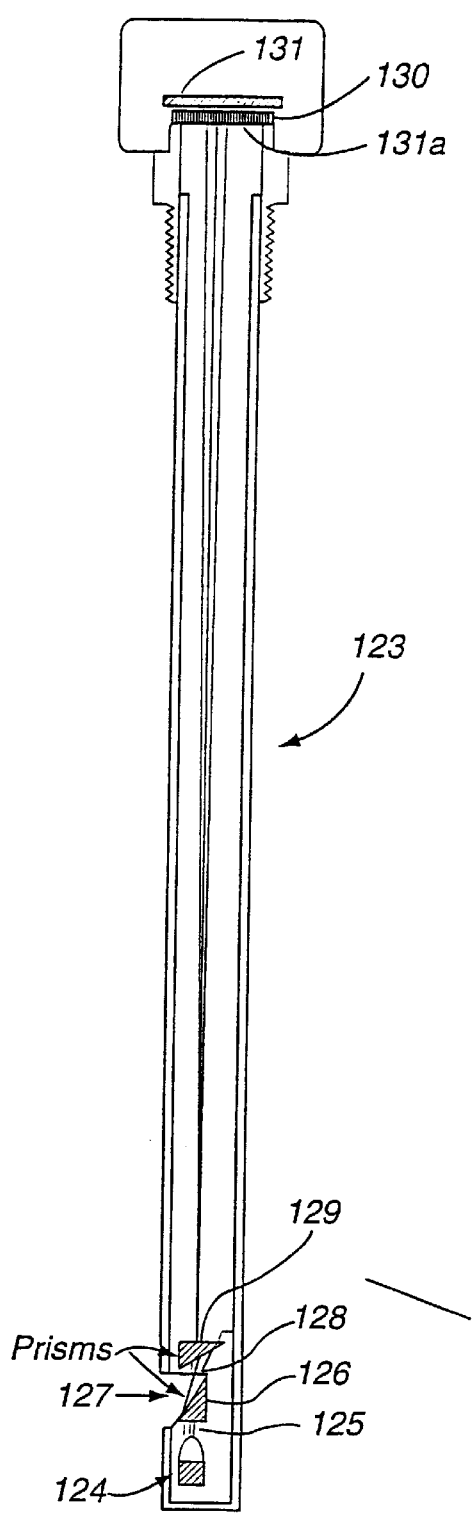
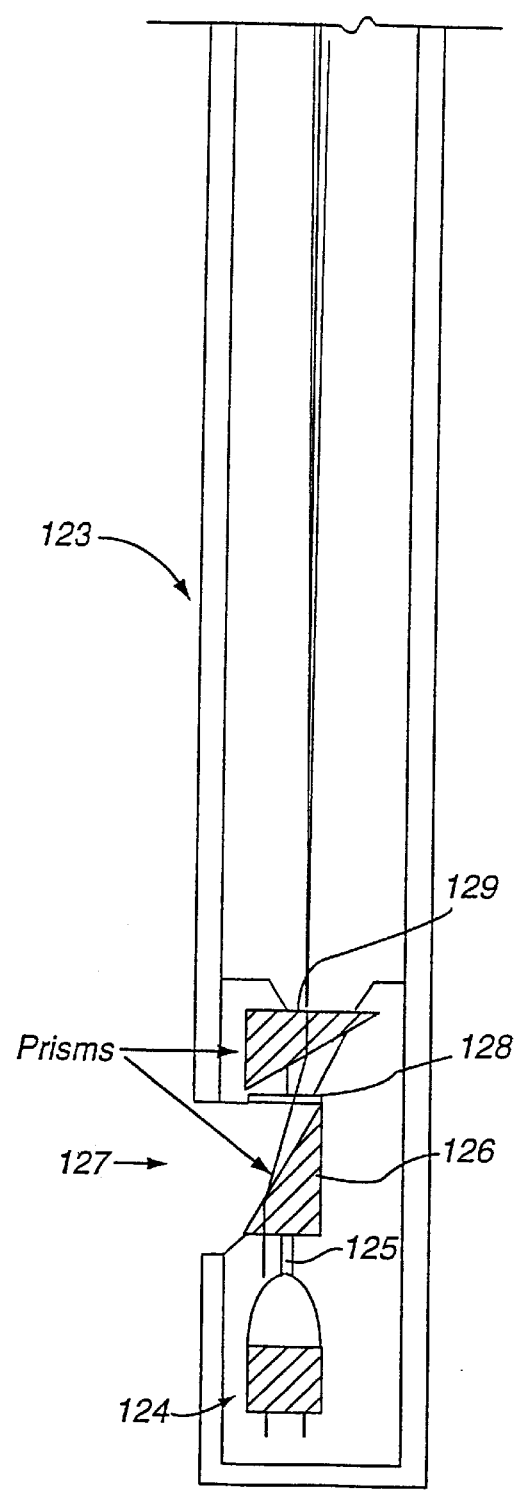
Fig. 7B　　　Fig. 7C

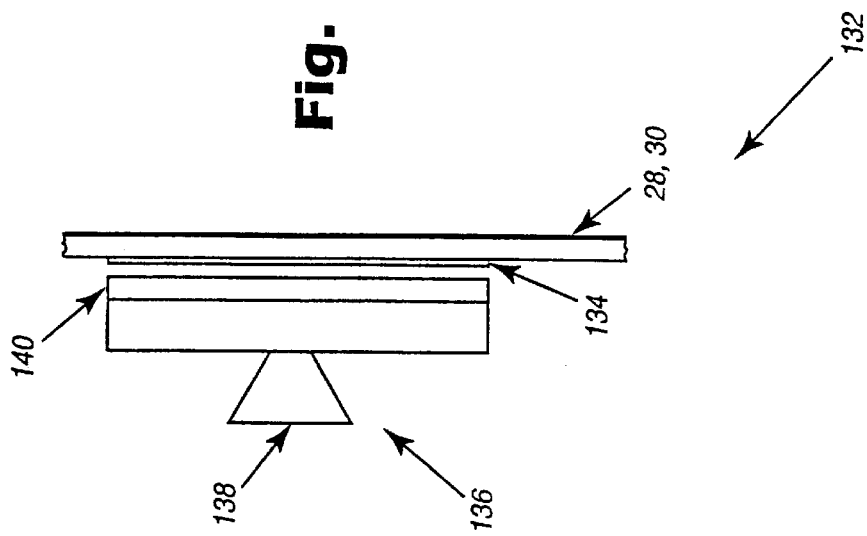
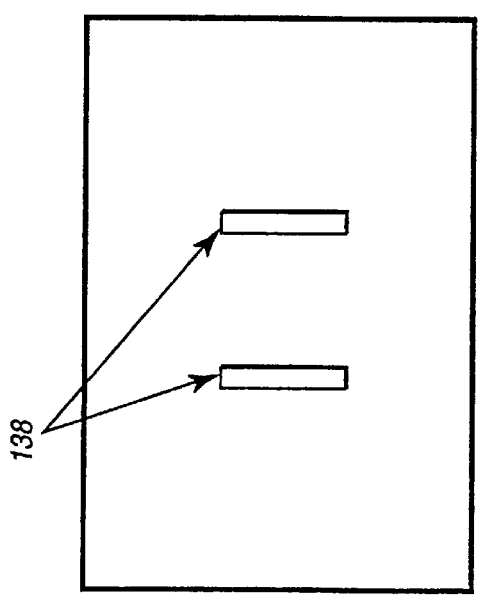
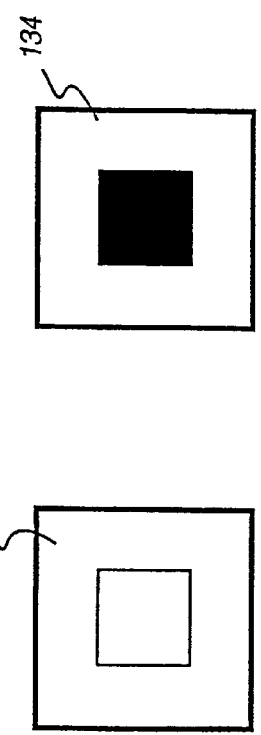

The Structure of PLURONIC® Surfactants

The Structure of PLURONIC® R Surfactants

The Structure of TETRONIC® Surfactants

The Structure of TETRONIC® R Surfactants

ENDOSCOPE REPROCESSING AND STERILIZATION SYSTEM

This application claims the benefit of U.S. Provisional Application Ser. No. 60/102,663, which was filed Oct. 1, 1998, the disclosure of which is incorporated herein by this reference. This application also claims the benefit of U.S. Provisional Application Ser. No. 60/102,664, which was filed Oct. 1, 1998, the disclosure of which is incorporated herein by this reference. This application also claims the benefit of U.S. Provisional Application Ser. No. 60/117,401, which was filed Jan. 27, 1999, the disclosure of which is incorporated herein by this reference.

BACKGROUND OF THE INVENTION

1. Field of the Invention

The invention generally relates to the field of reprocessing medical equipment. In particular it relates to an improved device and method for sterilizing and reprocessing endoscopes and will be described with particular reference thereto. The invention also relates to an improved device for sterilizing and reprocessing endoscopes in combination with a novel fast acting room temperature sterilant and methods of using the same.

2. Description of the Related Art

Sterilization connotes the absence of all life forms, including bacterial endospores which are the living organisms most resistant to conventional sterilants. Disinfection, by distinction, only connotes the absence of pathogenic life forms. Microbial decontamination is generic to both sterilization and disinfection.

Medical equipment is often sterilized at high temperatures. Commonly, the equipment is sterilized in a steam autoclave under a combination of high temperature and pressure. While such sterilization methods are very effective for more durable medical instruments, more sensitive medical instruments formed of rubber and plastic components with adhesives are wholly unsuited to the high temperatures and pressures associated with a steam autoclave. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and pressures. Further, endoscopes present particular problems in that such devices typically have numerous exterior crevices and interior lumens which can harbor microbes and thus be difficult to clean and sterilize using ordinary techniques. Therefore, the employment of a fast acting, low corrosivity sterilant is more desirable for reprocessing sensitive instruments, such as endoscopes.

Early efforts to sterilize more sensitive medical instruments, such as endoscopes, have met with limited success and all conventional methods have associated problems or detractions. Sensitive medical instruments, such as endoscopes, are often sterilized with ethylene oxide, which is thermally less severe than steam. The endoscope must be exposed to the ethylene oxide for a relatively long period, on the order of three and a half hours. Thereafter, eight to twelve hours are normally required for de-gassing or desorbing the ethylene oxide from plastic and other materials which are capable of absorbing the ethylene oxide. The pressurization and depressurization cycles of ethylene oxide sterilization may damage lens systems and other delicate instruments which are commonly integral with endoscopes. Moreover, the ethylene oxide is relatively expensive. It is sufficiently toxic and volatile that extensive precautions are commonly taken to assure operator safety. Therefore, the employment of a fast acting, low corrosivity sterilant which is nontoxic and preferably biodegradable for easy disposal would be more desirable for reprocessing sensitive instruments, such as endoscopes. Other medical or dental instruments which have lumens, are also in need of a method of cleaning and sterilizing which employs an effective device and sterilant which will not harm sensitive components and materials. Further, the need exists for a reprocessing system having a shorter reprocessing time cycle.

Liquid systems are commonly used for disinfecting endoscopes and other heat sensitive and delicate instruments. Using liquid sterilants or disinfectants to achieve disinfection is normally rapid, cost-effective and does minimal damage to the medical devices. Commonly, a technician mixes a sterilant composition and manually immerses the item to be disinfected. The immersion is timed by the technician. Technician variation in the mixing, timing, and equipment handling raises problems of assurance and reproducibility of the manual disinfection process. Rinsing of the items to remove chemical residues also adds a variable that reduces the assurance of disinfection or sterility. Once, rinsed, the disinfected endoscope or other item is susceptible to recontamination by airborne microbes. Conventional liquid systems require complete immersion of the endoscope in the liquid solution. Large and bulky items such as endoscopes require large immersion containers and equally large volumes of expensive sterilant or disinfecting solution. Further, merely soaking endoscopes in a sterilant or disinfectant is unacceptable since numerous pockets exist within the tubing that the sterilant or detergent cannot reach effectively. This leaves areas of contamination within the endoscope. With the prevalence of highly contagious diseases such as Hepatitis B and Acquired Immune Deficiency Syndrome, effective sterilization, or disposal, of all medical tools becomes mandatory. Accordingly, an ineffective effort to sterilize endoscopes by merely soaking is unacceptable. For example, U.S. Pat. No. 5,091,343 discloses a liquid sterilization system which involves placing the instrument to be sterilized in a tray or cassette which is then covered and positioned within a liquid sterilization unit. Within the unit the cassette or tray is filled with liquid sterilant, rinsed with a sterile rinse water and the rinse water drained away. As the rinse water is drained away, sterile air is introduced into the cassette or tray. The cassette or tray is removed from the unit and the process is completed with uncovering the instrument and removing it for storage or use. A major drawback of this type of process is the lack of assurance of a sufficient flow of sterilant and rinse water through the interior passages of the instrument. The low pressure circulation of the liquid sterilant in the cassette or tray and the numerous pockets inherent in such a tubular instrument provides no assurance that adequate sterilization is attained in the interior passages of the instrument. The exterior surfaces of instruments, such as endoscopes, typically have multiple connectors and branches which can define small crevices or niches harboring microbes. Because of this, low pressure circulation liquid sterilization systems, which rely on complete submersion of the endoscope, may also be inadequate to assure complete sterilization of all exterior surfaces.

Further, conventional systems for sterilization of endoscopes are designed to operate on a solitary cycle; that is, once the sterilization process has been initiated, it must be completed before a second instrument can be reprocessed and sterilized. This limitation results in unnecessary delays and severely restricts the capacity of a system for reprocessing instruments.

A need therefore exists to provide a device which can be used in combination with a fast acting, low corrosivity sterilant to effectively reprocess and sterilize complex medical instruments with lumens, in particular, such as endoscopes.

SUMMARY OF THE INVENTION

It is an object of the present invention to provide an improved device for the reprocessing and sterilization of medical instruments with lumens, such as endoscopes.

It is another object of the present invention to provide an improved device for reprocessing and sterilizing medical instruments with lumens, such as endoscopes in combination with a fast acting, non-toxic, low-corrosivity, sterilant that is capable of sterilizing objects containing microbes, such as bacterial spores.

It is another object of the present invention to provide an improved device which can effectively reprocess and sterilize more than one endoscope asynchronously.

BRIEF DESCRIPTION OF THE DRAWINGS

These, as well as other objects and advantages of this invention, will be more completely understood and appreciated by careful study of the following more detailed description of a presently preferred exemplary embodiments of the invention taken in conjunction with the accompanying drawings, in which:

FIG. 4A is a perspective sectional view of a first embodiment of a heater assembly, partly broken away to reveal the heater components, for use in the reprocessing device according to the principles of the present invention;

FIG. 5 is a front elevational view of the movable cassette assembly of a medical instrument reprocessing device according to the principles of the present invention;

FIGS. 7A–7C show a chemical concentration detector of the medical instrument reprocessing device according to the principles of the present invention;

FIGS. 8A–8D show a chemical sterilant container validation sensor system of a medical instrument reprocessing device according to the principles of the present invention;

DETAILED DESCRIPTION OF THE INVENTION

Device:

For ease of understanding the reprocessing device provided in accordance with the present invention, a preferred embodiment thereof will be described in detail. While the preferred embodiment of the present invention is intended to provide an improved device for reprocessing and sterilizing endoscopic devices, a fast acting room temperature sterilant, and a method of using the same in combination to reprocess and sterilize endoscopic devices, it is within the conception of the invention to adapt the invention to also reprocess and sterilize a variety of medical instruments, to include other types of medical instruments having a lumen, such as, for example, catheters.

Figure 1:
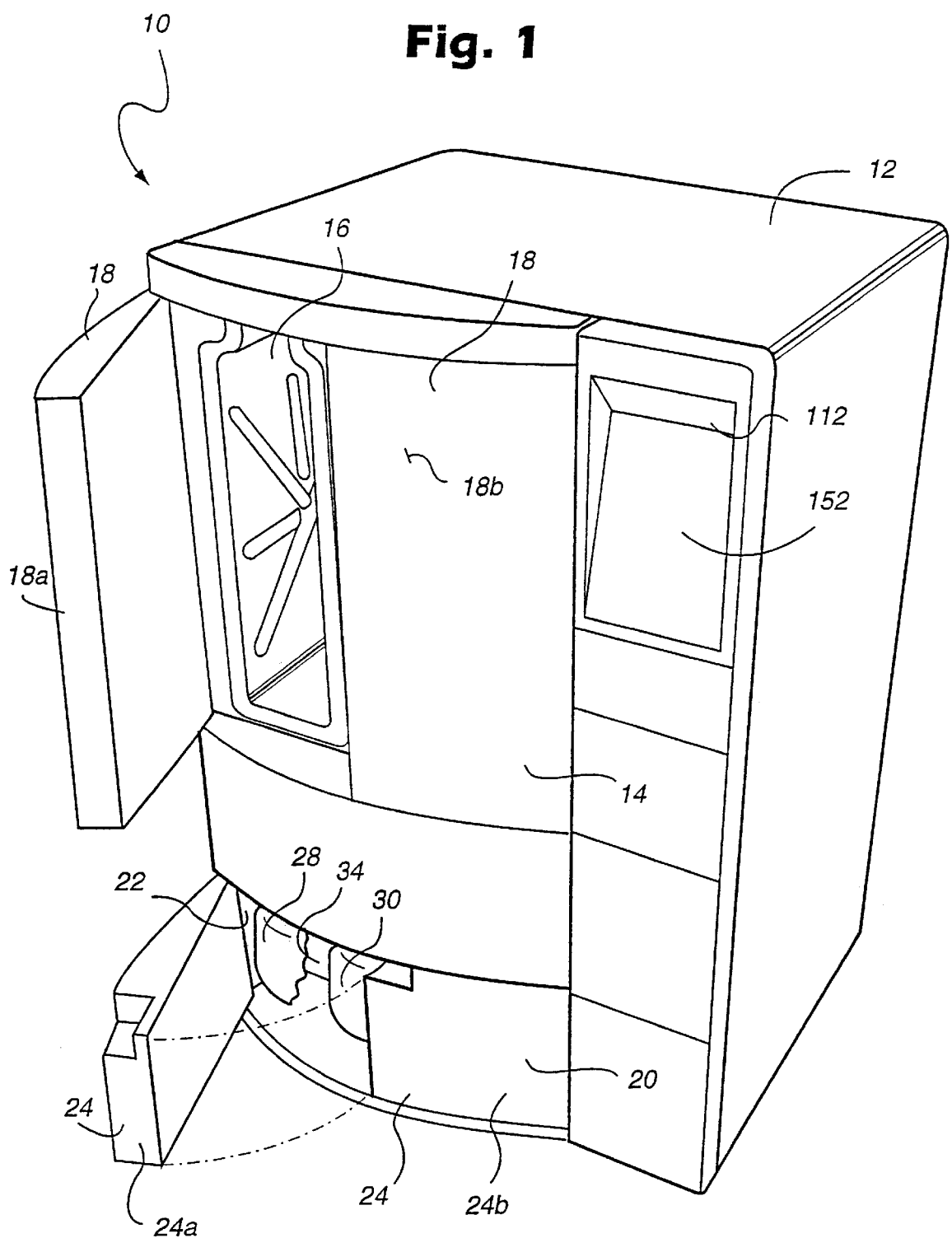
FIG. 1 is an exterior perspective view of a medical instrument reprocessing device according to the principles of the present invention having one of a pair of chemical supply drawer access doors in an open position and one of a pair of reprocessing bay cabinet access doors in an open position.
Figure 2:
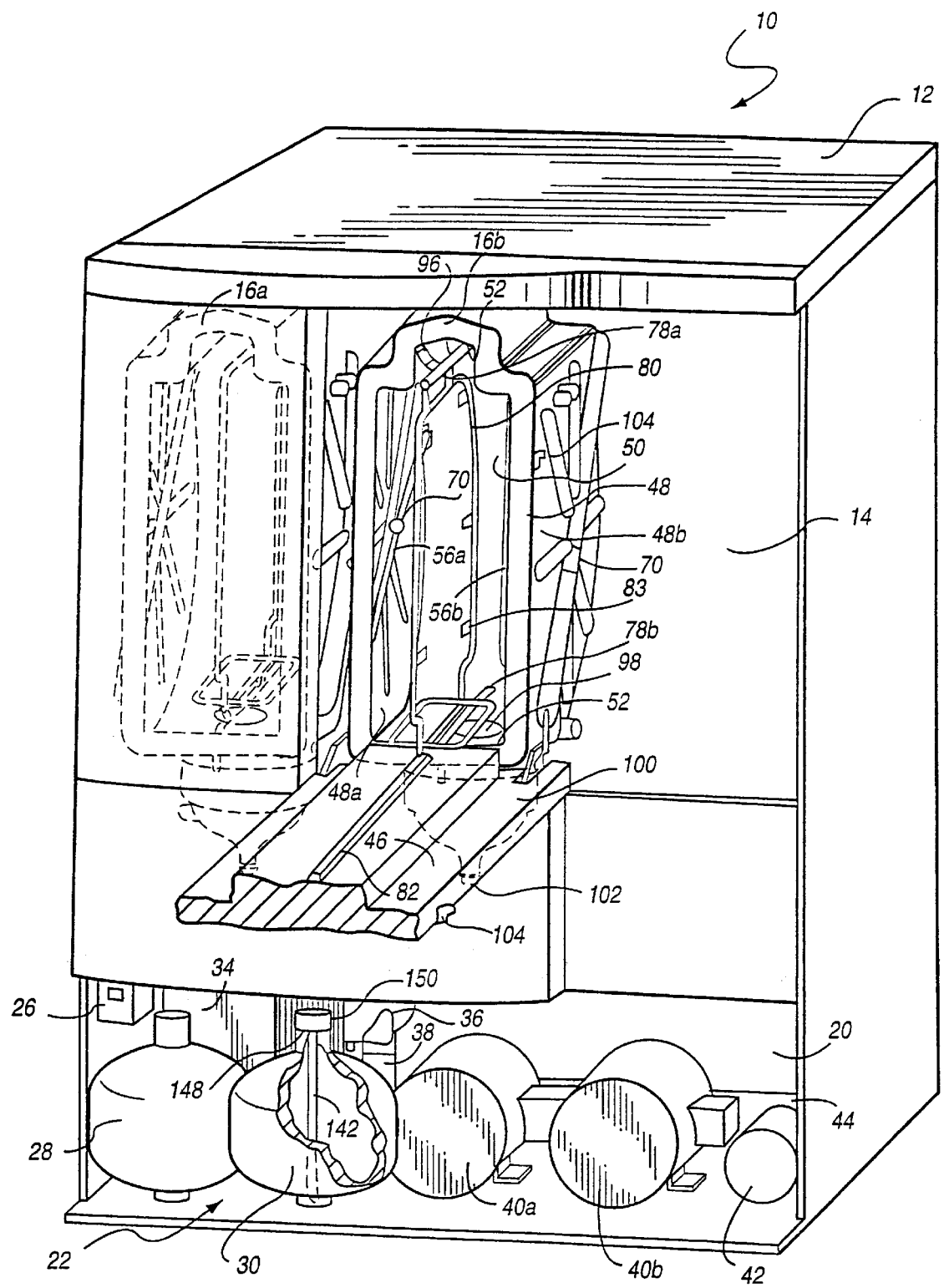
FIG. 2 is a perspective view of the major components of a medical instrument reprocessing device according to the principles of the present invention in one possible arrangement relative to each other and positioned in a representation of the compartmentalization provided by an exterior housing. Two reprocessing bays are represented in the reprocessing bay cabinet of the housing; one configured with a reprocessing bay door in the open position and the other, presented in broken lines, configured without the necessary reprocessing bay door.

Referring now to FIGS. 1–5, an endoscope reprocessing and sterilization system according to the principles of the present invention is shown and generally indicated at 10. An exterior housing 12 is provided to arrange, contain and provide protection for the components of the reprocessing system 10. A reprocessing bay cabinet 14 of the housing 12 is configured to contain at least one reprocessing bay 16. The reprocessing bay cabinet 14 is equipped with at least one cabinet access door 18. The embodiment shown in FIG. 1 is configured to have two cabinet access doors 18*a*, 18*b* which are shown with one cabinet access door 18*a* in the open position allowing access to the at least one reprocessing bay 16 and the other cabinet access door 18*b* in the closed position. The preferred embodiment shown in FIGS. 1–2 is configured to have two independently operated reprocessing bays 16*a*, 16*b*, although the concept of the present invention is not limited to two independently operated reprocessing bays 16.

A chemical supply drawer 20, which is configured to contain support components, generally indicated at 22, is equipped with at least one drawer access door 24. The embodiment shown in FIG. 1 is configured to have two chemical supply drawer access doors 24*a*, 24*b* which are shown with one drawer access door 24*a* in the open position allowing access to the support components 22 and the other drawer 20 access door 24*b* in the closed position. The support components 22, contained within the chemical supply drawer 20, can include a soap container 26, a plurality of chemical sterilant component containers 28, 30, a water heater 32, a hot water tank 34, a reaction chamber 36, a load sensor 38, an electric motor and pump 40, an air compressor 42, and a compressed air tank 44. The preferred embodiment shown in FIG. 2 is configured with two chemical sterilant component containers 28, 30 which serve to contain the two components of the multi-component concentrate system of the present invention as described herein. It is, however, within the concept of the present invention to configure the reprocessing system 10 to include a greater or lesser number of chemical sterilant component containers depending upon the number of components required for the sterilant used. In the preferred embodiment, each of the two reprocessing bays 16a, 16b is independently operated. To support such independent operation, the device of the present invention 10, as shown in FIG. 2, may be equipped with an independently operated electric motor and pump 40a, 40b, one for each reprocessing bay 16a, 16b.

Figure 6:
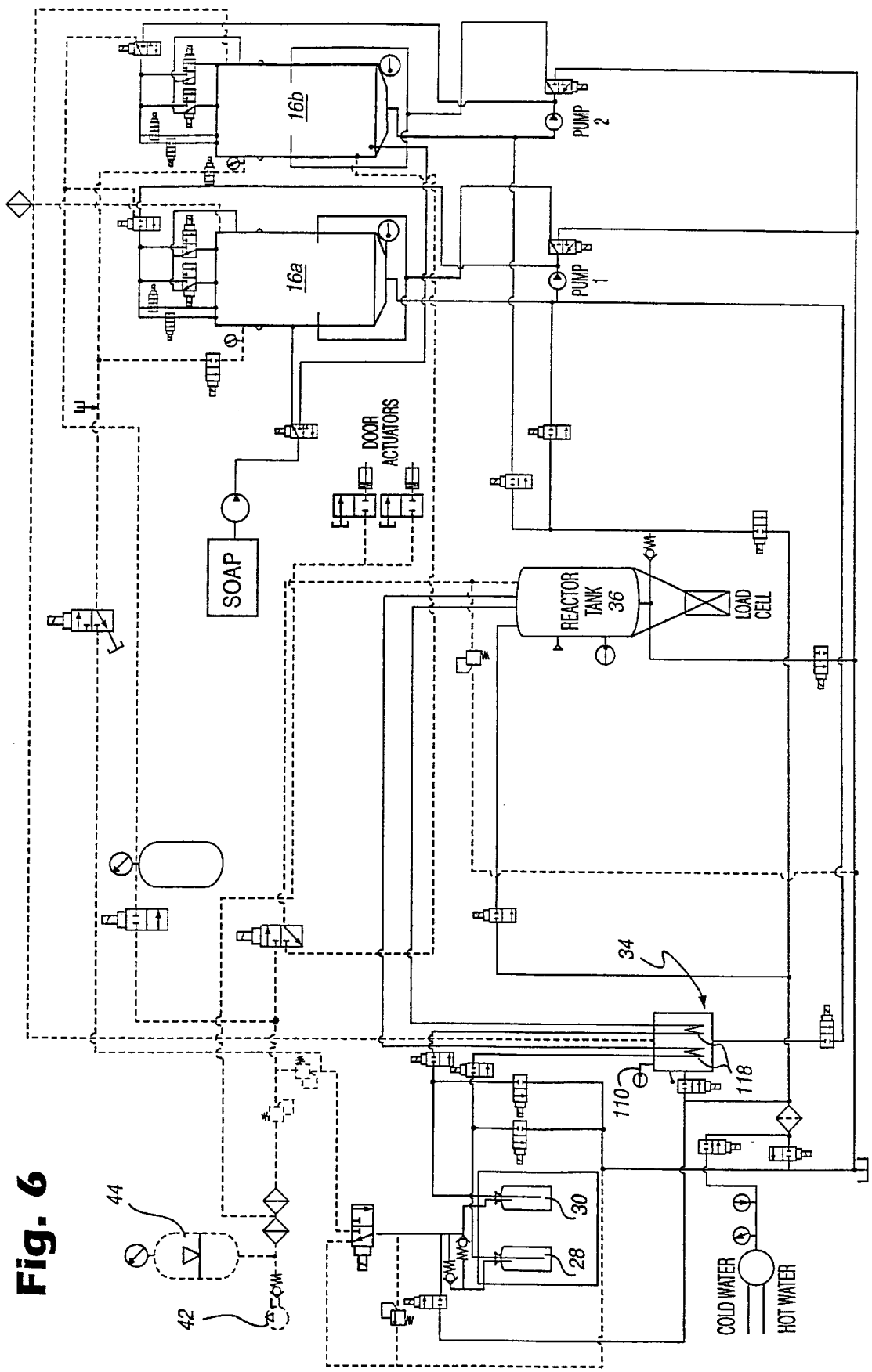
FIG. 6 is a schematic representation of the hydraulic system and pneumatic system of a medical instrument reprocessing device according to the principles of the present invention.

Hydraulic and pneumatic connections between each of the components contained within the chemical supply drawer 20 and the reprocessing bays 16a, 16b contained within the reprocessing bay cabinet 14 are shown only in FIG. 6 to simplify presentation of the major components shown in FIGS. 1–5.

The reprocessing bays 16a, 16b are identically configured and independently operated. Detailed discussion of the reprocessing bay components and operations will, for demonstration purposes, be limited to descriptions of reprocessing bay 16b.

The reprocessing bay 16b is equipped with a reprocessing bay door 46 which serves to seal the reprocessing bay during operation. The reprocessing bay door 46 can be constructed so as to provide thermal and sound proofing features. The vertical side walls 48a, 48b, back wall 50, ceiling member 52, and floor member 54 can also be formed to provide thermal and sound proofing features. The thermal and sound proofing features can be provided by manufacturing the side walls 48a, 48b, back wall 50, ceiling 52, floor 54, and door 46 structures of materials such as, for example, plastics, steel, glass, and the like. Additionally the side walls 48a, 48b, back wall 50, ceiling 52, floor 54 and door 46 members can be formed as solid or hollow members and the interior portion of hollow member(s) can be filled with thermal and/or sound insulating materials which are well known in the art.

Figure 3:
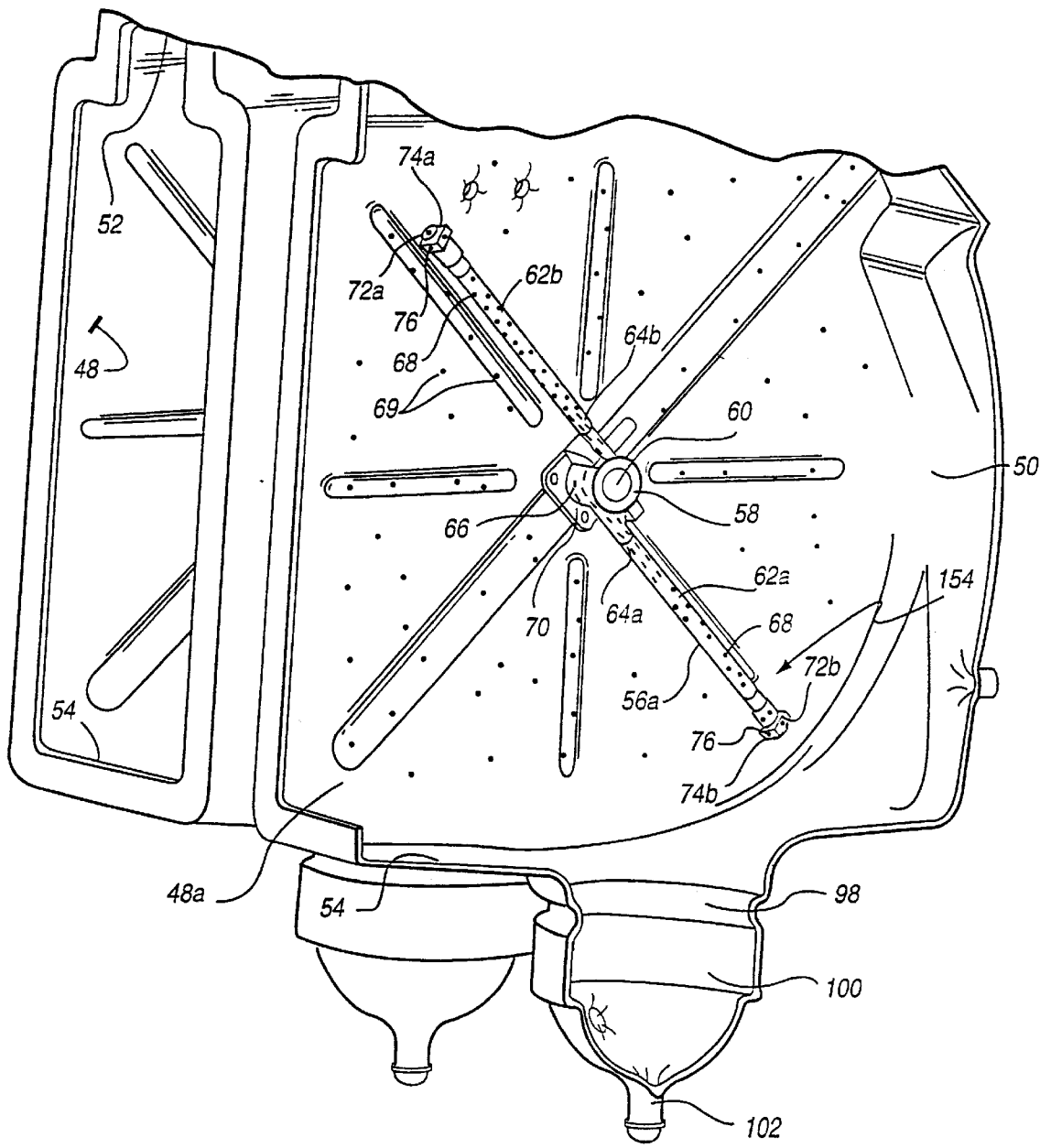
FIG. 3 is a perspective view of two reprocessing bays, without access panels, of a medical instrument reprocessing device according to the principles of the present invention. One reprocessing bay is shown in a partial sectional view disclosing an exterior pressure washing assembly.

The reprocessing bay 16b is equipped with at least one and preferably two identical rotating arm members 56. In the preferred embodiment, the two rotating arm members 56a, 56b are separately rotatably mounted to a central portion of opposing side walls 48a, 48b. The following detailed description applies to all rotating arm members 56 but reference is limited to rotating arm member 56a which is best shown in FIG. 3. The rotating arm member 56a includes a central hub sleeve 58 rotatably connected around a rotating arm hub member 60 which extends outwardly from and substantially perpendicular to the central portion of side wall 48a. At least two counterbalanced spray arms 62a and 62b are connected on approximate opposing sides of the central hub sleeve 58. Each spray arm 62a, 62b defines a spray arm lumen 64a, 64b (shown in part with broken lines). The spray arm lumens 64a, 64b extend at least a portion of the length of the spray arms 62a, 62b and serve to operatively connect a hub sleeve lumen 66 defined within the central hub sleeve 58 with a plurality of spray jets 68 defined in the wall of the spray arms 62a, 62b. Together the interconnected hub sleeve lumen 66, spray arm lumens 64a, 64b and spray jets 68 provide a conduit for the pressurized flow of washing, rinsing and sterilizing fluids from a rotating fluid connector 70, defined within the hub member 60, to the interior of the reprocessing bay 16b. The washing, rinsing and sterilizing fluids are provided to the rotating fluid connector 70 by tubular conduits as shown in FIG. 6. Optionally, one or more of the side walls 48a, 48b, back wall 50, ceiling 52, floor 54 and door 46 members walls of the reprocessing bay can be provided with wall spray jets 69 which are fluidly connected to the rotating fluid connector 70 or, alternatively, to a separate fluid inlet connector. Tubular conduits used in the present invention can be formed of metal, plastic, glass and the like, as is well known in the art.

At each distal end 72a, 72b of spray arms 62a, 62b is a spray nozzle 74a, 74b each configured with a plurality of spray openings 76. The spray openings 76 are operatively connected to the spray arm lumens 64a, 64b and together with the spray jets 68 direct sterilant and rinse fluids into the central portion of the reprocessing bay 16b. Alternatively, spray nozzles 74a, 74b may also rotate about the longitudinal axis of spray arms 62a, 62b. In addition to the fluid directing function for sterilizing and rinsing, the spray openings 76 and spray jets 68 direct the pressurized flow of fluid out of the spray nozzle 74a, 74b and spray arms 62a, 62b in such a manner as to effect aggregate impulse which produces a reactive rotational force of the spray arms 62a, 62b around the central hub 60.

The reprocessing bay 16b may have at least one cassette guide which serves to guide a cassette 80 from a loading and unloading position outside of the reprocessing bay 16b to an operational position inside the reprocessing bay 16b. The reprocessing bay 16b may be equipped with two cassette guides, an upper cassette guide 78a and a lower cassette guide 78b. The upper cassette guide 78a can be secured to the ceiling 52 or alternatively to the upper portion of the back wall 50 of reprocessing bay 16b or incorporated into the bay design. The lower cassette guide 78b can be secured to the floor 54 or alternatively the lower portion of the back wall 50 of reprocessing bay 16b or incorporated into the bay design. The interior surface of the door 46 of reprocessing bay 16b may be configured to have a door guide 82 which aligns with the lower cassette guide 78b to facilitate the positioning of the cassette 80 into or out of the reprocessing bay 16b.

The cassette 80 is configured to removably secure a medical device such as an endoscope within the reprocessing bay 16b. The medical device is preferably suspended above the washing, rinsing or sterilizing fluid. The cassette 80 can be equipped with a plurality of clamping members 83 for holding the medical device being sterilized in position in the reprocessing bay 16b. The cassette can be removably positioned in the reprocessing bay 16b in a suspended orientation to the upper cassette guide 78a. As best shown in FIGS. 2 and 5, the cassette is preferably removably positioned between the upper cassette guide 78a and the lower cassette guide 78b. As best shown in FIG. 5, the cassette 80 may have an upper rotational member 86 and a lower rotational member 88 which are disposed to freely rotate about respective axle members 90a, 90b which are fixedly secured to the upper and lower portions of the cassette 80, respectively. The upper rotational member 86 and the lower rotational member 88, hereinafter referred to as wheels, are each provided with a guiding groove 92, 94, respectively. The guiding grooves 92, 94 are sized and configured to complement the size and shape of the upper cassette guide 78a and the lower cassette guide 78b, respectively, for facilitating movement of the cassette into and out of the reprocessing bay 16b. In addition, the guiding groove 94 may be sized and configured to complement the size and shape of the door guide 82 so as to guide and facilitate movement of the lower rotational member 88 across the inner surface of the reprocessing bay door 46 when the bay door 46 is in the open position.

Extending into the upper portion of the reprocessing bay 16b is a medical device connector 96 which is configured to provide a fluid tight fitting for a wide variety of medical devices, such as endoscopes. It is within the concept of the present invention to provide connection adapters which will permit a fluid tight fitting during pressure sterilization of the lumen of a wide variety of medical devices. Washing, rinsing and sterilizing fluids are provided to the medical device connector through tubing conduits as shown in FIG. 6.

The floor member 54 of the reprocessing bay 16b is configured to serve as a reservoir 98 for collection of fluids which have been sprayed onto or pumped through the medical device being reprocessed and sterilized in the reprocessing system 10. The reservoir can be equipped with a filtration system 100 of at least two levels of filtration. A sump drain 102 for collection of fluids is provided in the lower portion of the reservoir 98. The size of the reservoir 98 and the vertical positioning of the reprocessing bays 16 allows the reprocessing system 10 to operate and recirculate about 2–5 liters of fluid. The reprocessing system 10 preferably operates with about 3 liters of sterilant.

In operation of the reprocessing system 10, the reprocessing bay door 46 can be selectively secured by at least one latch assembly 104. A safety feature can be provided which will halt operation of the reprocessing system 10 upon opening of the latch assembly 104. Alternatively, the ability to unlatch the latch assembly 104 during operation of the reprocessing system 10 can be disabled until completion of the selected operating cycle.

As best shown in FIGS. 2 and 4 and operationally described in FIGS. 6–9, the support components 22 located in the chemical supply drawer 20 facilitate preparation and supply of the fluids used in the reprocessing bays 16 during operation of the reprocessing system 10.

The support components 22, contained within the chemical supply drawer 20, can include a soap container 26 which provides soap to the reprocessing bay 16b as required by the cycle selected.

In the preferred embodiment, as best shown in FIG. 2, two chemical sterilant component containers 28, 30 are provided. As will be later described in detail, in the preferred embodiment the sterilant used in the reprocessing bay(s) is a muti-component concentrate system and most preferably is a two component concentrate system which, for best performance, is stored in separate component containers 28, 30 until just prior to use. The concept of the invention is not limited to two components but can be adapted as necessary to accommodate a sterilant requiring one, two or more components by merely configuring the device for the appropriate number of component containers.

As shown in FIG. 4A, in a first embodiment, a water heater and a hot water tank are further provided in the reprocessing system of the invention for heating water for use in the reprocessing cycle and/or for heating the sterilant or sterilant components therefor. In that regard, the sterilant or sterilant components used in the reprocessing cycle of the invention, discussed in greater detail below, are caustic. Thus the sterilant or sterilant components are flowed through a closed conduit system to and among the components of the reprocessor. Furthermore, the temperature of the sterilant components may be maintained at an elevated level prior to delivery to the reactor 36 and the temperature of the sterilant may be maintained at an elevated level prior to delivery to the reprocessing bay(s). To do so, the tubing through which the sterilant or sterilant components flow preferably passes through the hot water tank to define a heat exchanger. Thus, in accordance with a first embodiment, shown in FIG. 4A and described in greater detail below, the heater and tank are provided as a combination unit with coiled tubing for heat exchange disposed therein. When combined, the heater and hot water tank can serve multiple purposes. First, the water heater can be used for heating water which is subsequently used in the soap cleaning phase of the reprocessing cycle as well as in the sterilant dilution phase of sterilant preparation in the reaction chamber 36. The water heater and hot water tank can also be used as a heat exchanger to heat the sterilant components during transfer to the reaction chamber 36 and/or, subsequently, to maintain the sterilant at the optimum operating temperature prior to use. As yet a further alternative, however, the reprocessing system 10 can be adapted to operate with room temperature fluids thus eliminating the need for the water heater and hot water tank.

With reference to FIG. 4A, a first embodiment of a combined heating coil 32 and hot water tank 34 is shown. More particularly, the assembly includes a water tank 106 which serves to contain and insulate water pumped into and heated in the hot water tank 34. A controlled heater element 108 is provided to initially heat and thereafter maintain the temperature of the water in the water tank 106. A temperature probe 110 is provided to measure the temperature of the water in the tank and transmit that information to a central processor 112. An inner tank valve 114 is provided on the upper surface of an inner tank 116. The inner tank valve 114 may be temperature sensitive or preferably is controlled by the central processor 112 from information received from the temperature probe 110. The inner tank 116 is configured to enclose sterilant component containing coils 118 which act as conduits to transport the sterilant components to the reaction chamber 36 creating sterilant then on to the reprocessing bay 16b. An upper rim 120 of the inner tank 116 extends above the water level of the water tank 106 and serves to keep water from prematurely entering the inner tank 116. A water level sensor 122 is provided to determine the amount of water in the water tank 106. The water level information is provided by the water level sensor 122 to effect a cut off of water flow into the water tank 106. The water level sensor is configured to sense a high water condition and stop water flow into the water tank 106 prior to the water level going above the upper rim 120 of the inner tank 116. This protective feature is able to keep water that has not reached a target temperature or temperature range, which in the first embodiment is about 40° C. to about 55° C., from entering into the inner tank and undesirably cooling the coils 118 and sterilant or sterilant components contained therein to a temperature below the target range. In the embodiment illustrated in FIG. 4A, two coiled tubes 118 extend into the water tank 106, e.g. one for each sterilant component. When the temperature of the water in the water tank 106 reaches the most preferred temperature of e.g. about 40° C. to about 55° C., the inner tank valve 114 opens to permit the warm water to drain from the water tank 106 into the inner tank 116. The warm water fills the inner tank and serves to maintain the coils and enclosed sterilant or sterilant components at the most preferred operating temperature prior to mixing in the reaction chamber 36.

Figure 4B:
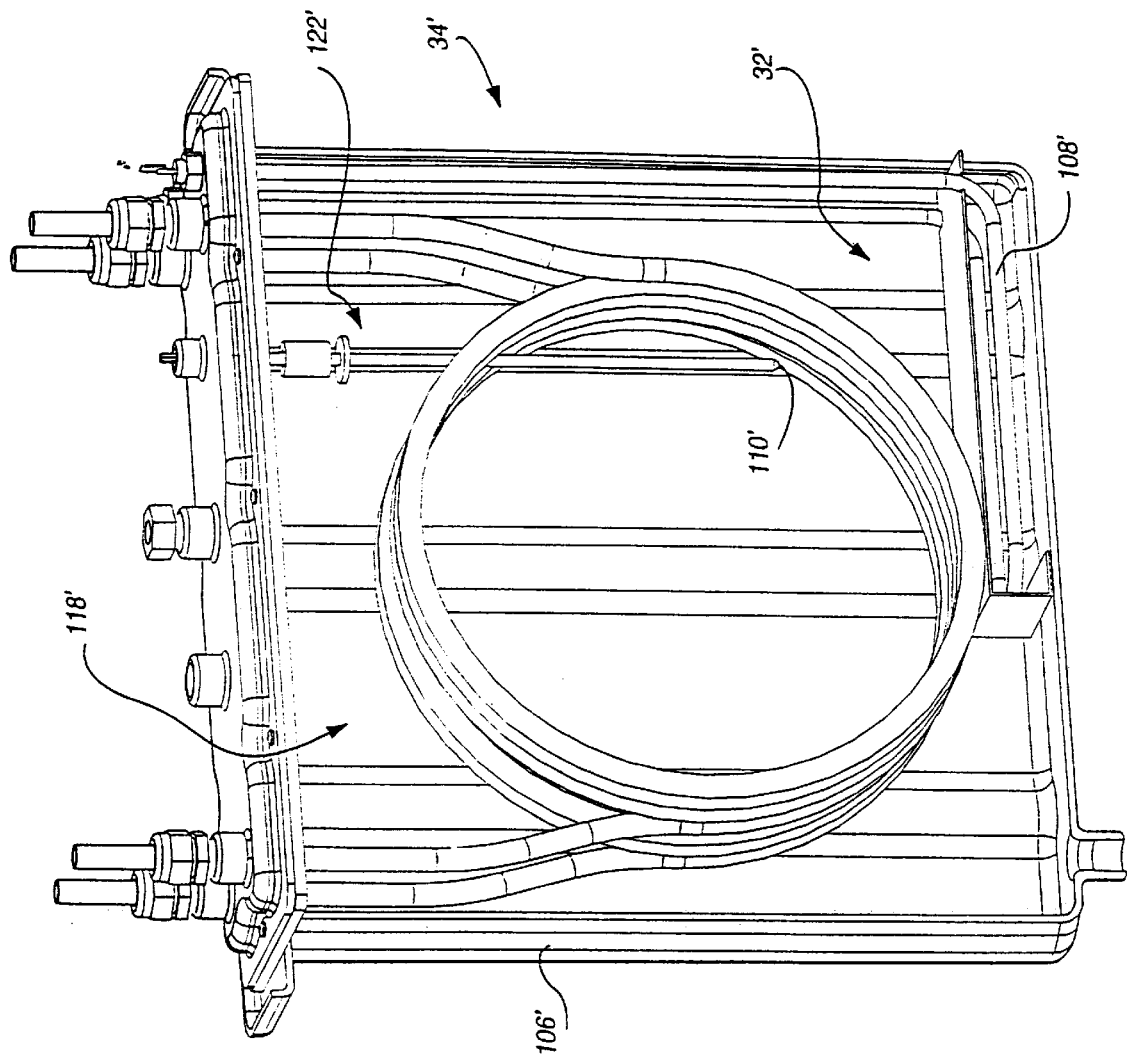
FIG. 4B is a perspective sectional view of a second embodiment of a heater assembly, partly broken away to reveal the heater components, for use in the reprocessing device according to the principles of the present invention.

With reference to FIG. 4B, a second, and presently preferred, embodiment of a combined heating coil 32' and hot water tank 34' is shown. More particularly, the assembly includes a water tank 106' which serves to contain and insulate heated water pumped into the hot water tank 34'. Heated water is received through a mixing valve that automatically mixes hot and cold water to obtain the desired temperature water. A controlled heater element 108' is provided to maintain the temperature of the water in the water tank 106'. A temperature probe 110' may be provided to measure the temperature of the water in the tank and transmit that information to a central processor 112. In contrast to the embodiment of FIG. 4A, no inner tank is provided in the hot water tank 34'. Thus, the fluid in the coiled tubes 118', which may be sterilant components prior to delivery to the reaction chamber 36 or sterilant prior to delivery to the reprocessing bay(s) 16a, 16b, will be heated according to the temperature of the water in the tank 106'. A water level sensor 122', such as a float switch, is further provided to effect a cut off of water flow into the water tank 106' or initiate flow thereto.

The reaction chamber 36 in the preferred embodiment of the present invention is positioned upon and supported by a load sensor 38. It is however with the concept of the invention to secure the reaction chamber 36 in the reprocessing system 10 by suspending it below a load sensor 38. The components of the sterilant of the present invention are provided to the reaction chamber 36 incrementally so as to enable the load sensor 38 to determine the precise amount of each component transferred to the reaction chamber 36 as the transfer takes place. In the preferred embodiment, the reaction of the sterilant components is allowed to take place after which, based upon the measurements obtained from the load sensor, the correct amount of water is weighed in to the reaction chamber 36 to properly dilute the sterilant prior to use. Accuracy of the load sensor 38 is critical to proper mixing of the components of the sterilant. The load sensor 38 of the present invention is configured to prevent shifting of the reaction chamber 36 from affecting the load sensor measurements. While some vertical movement is permitted and does not affect the load sensor measurements, the load cell of the present invention is configured to maintain horizontal stability, by a supporting strap located on top of the reactor vessel. The load cell of the present invention may be equipped with a test feature to ensure consistent and correct readings. The load sensor 38 may be checked for zero load when the reaction chamber 36 is empty. The load sensor 38 may also be checked against a known volume and weight of a specific volume of water, such as the volume of the inner tank 116.

The reprocessing system 10 preferably operates with sterilant temperatures from about 20° C. (room temperature) to about 50° C. Most preferred temperatures of the presently preferred embodiments are from about 40° C. to about 50° C. The sterilant components may be heated and reacted at higher temperatures. However, temperatures higher than about 50° C. in the reprocessing bay(s) may cause damage to the endoscopes. As noted above, temperature and/or level sensors can provide the information measurements to the central processor 112 and thus enable the automatic drainage and refilling of the inner tank throughout the selected cycles of operation of the reprocessing system 10, thus maintaining the temperature of the sterilant at a temperature of from about 40° C. to about 50° C.

Circulation of the various solutions used in different cycles of the reprocessing system 10 is performed by an electric motor and pump 40. It is however within the conception of the present invention to configure the device to use gravity flow for the transfer of some fluids in the reprocessing system, for example water flow to the reaction chamber for dilution of the sterilant. In the preferred embodiment of the present invention, each reprocessing bay 16a, 16b is provided with a dedicated electric motor and pump 40. It is however within the scope of the invention to configure the reprocessing system 10 such that the central processor 112 could effect a time sharing of electric motor and pump 40 assets for systems having a larger number of reprocessing bays than that of the preferred embodiment. However, time sharing would increase the overall processing time. Central processor 112 control of solution transfers throughout the selected cycles is effected by hydraulic conduit and valve systems known in the art; to include, for example the use of solenoid valves. FIG. 6 provides a detailed schematic of an exemplary hydraulic system of the preferred embodiment of the present invention.

In the preferred embodiment of the present invention, delivery of the components of the sterilant into the reaction chamber 36 is accomplished using compressed air. An air compressor 42, under control of the central processor 112 is provided for purpose of maintaining the air pressure in a compressed air tank 44. On command of the central processor 112, compressed air from the compressed air tank 44 is provided to the chemical sterilant containers 28, 30 in a programmed order so as to transfer each component to the reaction chamber 36 with the greatest precision. Alternatively, air pressure may be maintained on the chemical sterilant containers 28, 30 and instead the central processor 112 controls valving in a programmed order so as to transfer each component. The load sensor 38 controls the information input to the central processor 112 which in turn controls the output of the chemical sterilant containers 28, 30. FIG. 6 also provides a schematic of an exemplary pneumatic system of the preferred embodiment of the present invention.

Figure 7A:
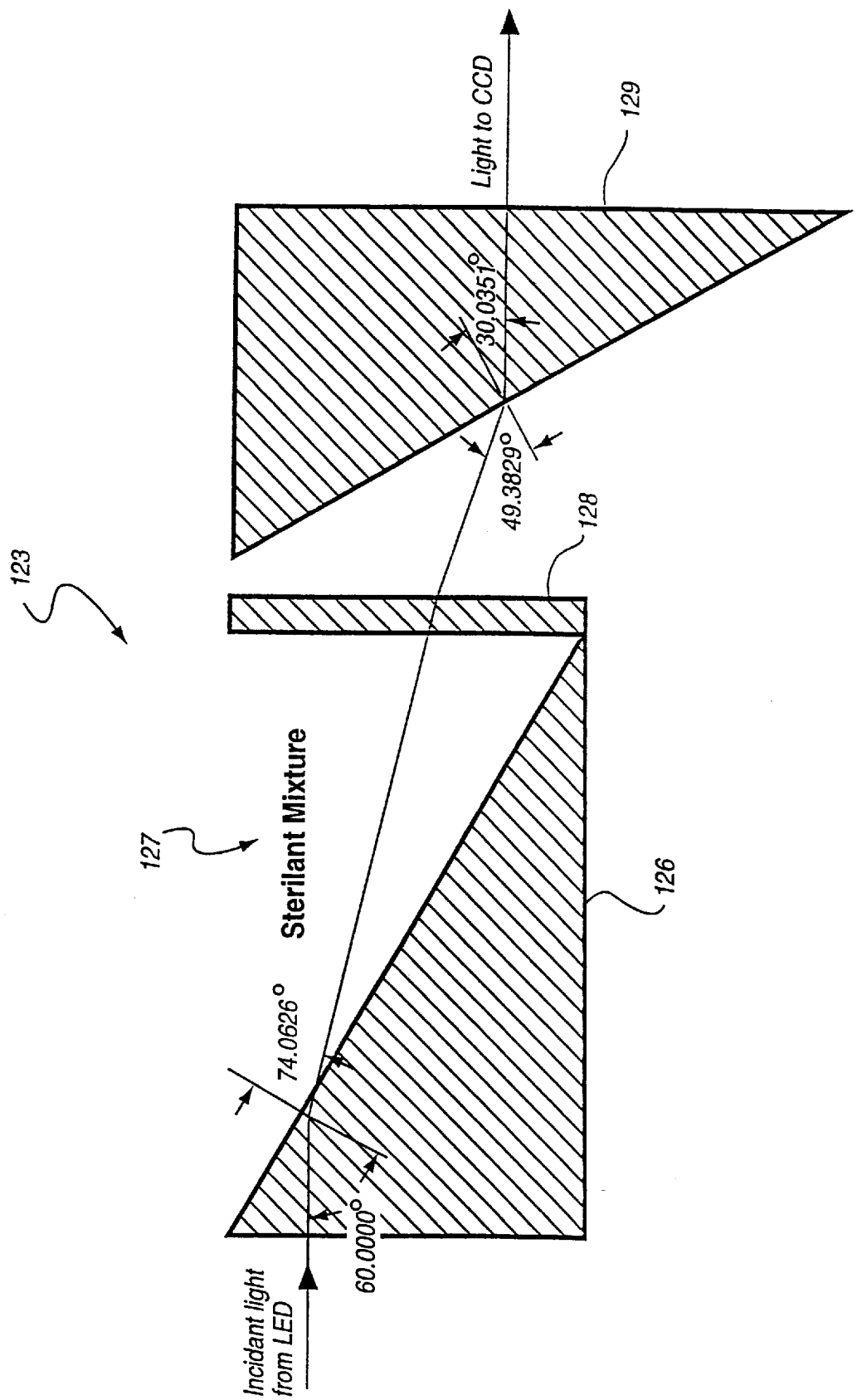

The present invention can be provided with a chemical concentration detector for determining the concentration of sterilant in the reaction chamber 36. A first embodiment of a suitable chemical concentration detector 123 is shown in FIGS. 7A–7C. A second, and presently preferred embodiment of a suitable chemical concentration detector 223 is shown in FIG. 7D, and described below with reference thereto.

Referring first to FIGS. 7A–7C, in accordance with a first embodiment, a deflection cell-type device is used for measuring chemical concentration of the sterilant because of its simplicity and low cost. In this embodiment, infrared light from a point-source LED 124 is passed through a slit 125 into the small end of a 30°–60°–90° prism 126. The hypotenuse of this prism is in direct contact with the sterilant by means of a small notch 127 near the end of the probe. The beam of light is deflected at this inner face by an amount proportional to the refractive index of the sterilant according to Snell's Law (see FIG. 7A). The beam passes through the sterilant and then exits through a simple transparent window 128 (PYREX for example). The light is then redirected up the axis of the probe by a second 30°–60°–90° prism 129 and onto a chemical concentration detector array (CCD) 130 (see FIG. 7B). The CCD 130 has a single row or array of a plurality of closely spaced pixels. As a non-limiting example, the detector can have about 100–140 pixels that are spaced on about 0.0125 $\mu$m centers. Small changes in the deflection of the light beam are amplified by the relatively long distance (for example greater than about 20 mm) which the light travels as it passes up the axis of the probe. The light beam forms a Gausian energy distribution on the linear array of pixels that form the CCD 130. A threshold comparator 131 is used to convert this distribution into a "boxcar" profile. The position of the edge(s) of this boxcar on the CCD 130 indicates the refractive index of the sterilant. The refractive index is sensitive to temperature at this relatively high resolution. The temperature of the prism/sterilant is measured with a thermistor and used to compensate the refractive index measurement. Because of the potentially aggressive nature of sterilant solutions, the materials that come into contact with the sterilant should be limited to glass, silicone-RTV (room temperature vulcanized), and chlorinated polyvinyl chloride (CPVC) and the like. The probe can be made of glass or similar material. The CCD 130 is very sensitive to any light in the visible and near infrared wavelength regions. The near infrared light source 124 (880 nm) combines with a longpass IR filter 131a over the CCD 130 to yield a source-detector pair that is very insensitive to ambient light fluctuations. The CCD 130 will receive different amounts of reflected light depending on the solutions refractive index. The light sensor information can be relayed to the central processor 112 where it will be interpreted to determine the concentration of the sterilant solution.

Figure 7D:
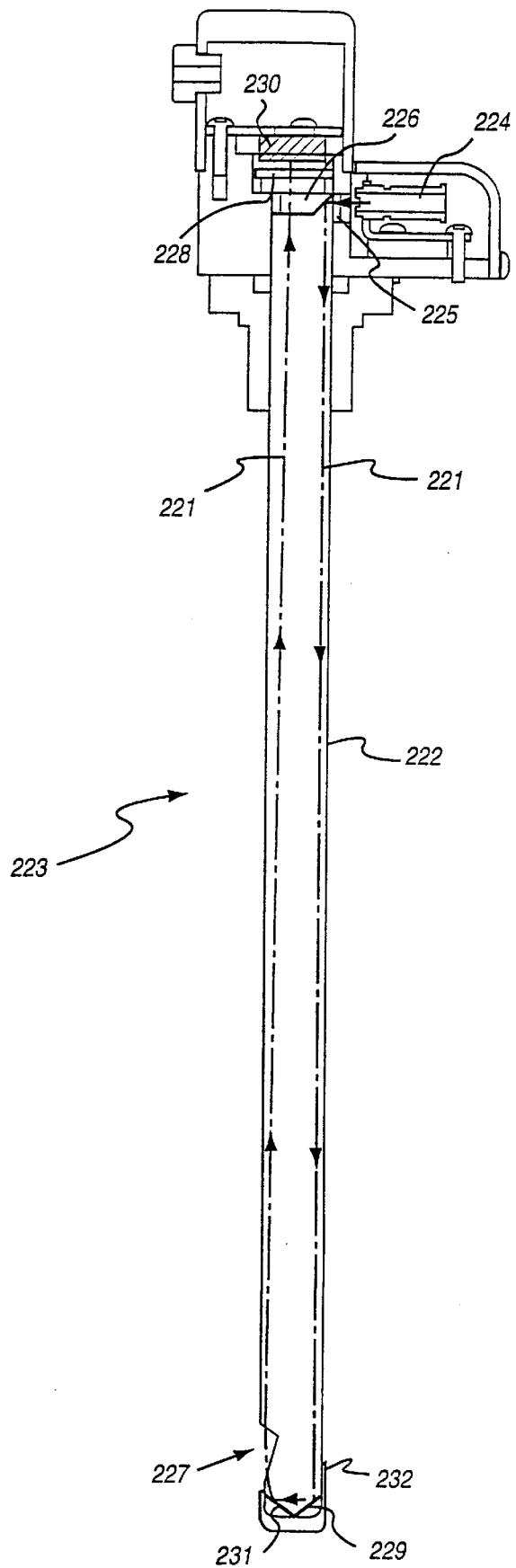
FIG. 7D shows an alternate chemical concentration detector of the medical instrument reprocessing device according to the principles of the present invention.

Referring now to FIG. 7D, a second embodiment of a chemical concentration detector 223 is shown. This chemical concentration detector also works by means of detecting the refractive index of the solution. The laser 224 shines a 5 mW 670 nm laser beam 221 through a line-generating lens 225. This light then enters the glass probe 222 of the detector 223. On the top of the probe a 45 degree prism 226 redirects the light 221 towards the bottom of the probe 222. The light traveling down the probe is then reflected horizontally by means of another 45 degree cut 229 located at the bottom of the glass probe. The light then is reflected toward the window or notch 227 of the probe by a further cut 231, which is approximately 53 degrees from vertical. The light then travels out of the probe 222 and through the chemical solution. The refractive index of the solution governs where the light 221 reenters on the top of the window 227 of the glass probe. The light then travels through the glass probe towards the top and leaves the glass probe. Next the beam 221 passes through a neutral density filter 228 to reduce the intensity of the light. This beam then is projected on to a CCD 230 which reads the horizontal position of the beam. This position is read by the CPU (not shown), which determines the refractive index of the solution. The remaining parts of the unit shown are used for housing the electronics and laser and for mounting the probe into the reactor. The cap 232 on the bottom traps air to permit the bottom two cuts 229, 231 to reflect the laser.

As best shown in FIGS. 8A–8D, the present invention can be provided with a chemical sterilant container validation sensor, generally shown at 132. The container validation sensor, 132 provides a system by which a user can validate that a correct chemical sterilant container 28, 30 has been placed into the reprocessing system 10. The container validation sensor, 132 also precludes the reuse of a chemical sterilant container 28,30. A heat sensitive label 134 can be attached to the chemical sterilant container 28, 30 at the time of manufacture. The label 134 can be visually identified as new by a distinctive color, for example, white. The chemical sterilant container 28, is placed in the reprocessing system 10 at a position in contact with a sensor assembly, generally shown at 136. The sensor assembly 136 includes an optical sensor 138 proximate to a heating pad 140. The optical sensor 138 can detect the presence of the chemical sterilant container 28, 30 and provide a signal to the central processor 112 to turn on the heating pad 140. The heating pad will warm the label 134 and cause the label 134 to turn a different color, for example, black. After a period of time, for example, about 10–30 seconds, the heating pad 140 will be turned off and the optical sensor 138 will not detect the presence of the originally colored label. Reprocessing will proceed if the container validation sensor 132 senses a change in the label color. Absent both conditions, the placement of a chemical sterilant container 28, 30 with a new unheated label 138 and a color change after an exposure of that label 138 to the heating cycle of the heating pad 140, an error message will be sent to the central processor 112 and the reprocessing system 10 will not operate. This safety device precludes operation of the reprocessing device 10 if there is an absence of a chemical sterilant container 28, 30 or if the chemical sterilant container 28, 30 inserted in the device has no label or if the chemical sterilant container 28, 30 inserted in the device has a black (used) label.

In addition to a validation sensor system 132, the present invention can include chemical sterilant containers 28, 30 which are designed to respond to pneumatic force for transfer of the components to the reaction chamber 36 and from the reaction chamber 36 to the reprocessing bays 16. As best shown in the cutaway portion of the chemical sterilant container 30 in FIG. 2, the design of the chemical sterilant containers 28, 30 includes an internally positioned straw tube sipper 142. The tube sipper 142 extends to the bottom of the chemical sterilant container 30 while the top of the sipper tube 142 fits into a straw header 144 which in turn fits into the neck 146 of the chemical sterilant container 30. When preparing the chemical sterilant container 30, the chemical component is filled into the chemical sterilant container 30 and a foil seal cap 148, which may include a vented membrane, is placed on the chemical sterilant container 30 and sealed with induction energy to prevent leaks. When preparing for use in the reprocessing system 10, the user removes the cap 148 exposing the membrane seal which is then punctured with a spike in the screw-on connector assembly 150. A gasket in the cap seals the connector assembly 150 to the chemical sterilant container 30. The spike of the connector assembly 150 makes two fluid connections to the chemical sterilant container 30, one concentric through the straw header 144 and the other eccentric outside the tube sipper 142. The spike of the connector assembly 150 is operationally connected to two tubing lines in the reprocessing system 10. The chemical is removed from the chemical sterilant container 30 by forcing air pressure into the chemical sterilant container 30 through the eccentric connection. This forces the chemical component up through the tube sipper 142 and into the tube running to the reaction chamber 36. When the chemical supply in the chemical sterilant container 30 is exhausted, the air supply tube is used to put water into the chemical sterilant container 30. This washes the top connection area as well as the chemical sterilant container 30 sides and tube sipper 142 to remove residual chemicals. This flushing process can be repeated as necessary to remove the residual chemicals from the chemical sterilant container 30.

In operation, the preferred embodiment of the present invention provides for asynchronous reprocessing of two endoscopes with overlapping cycle time periods. Chemical components for the sterilant are heated and measured as they are moved to and mixed in the reaction chamber 36. The sterilant temperature is monitored and controlled and the reaction of the chemical components in the reaction chamber 36 is timed under the control of a central processor 112. The sterilant's refractive index is measured to verify the presence of the sterilant. Water is added to dilute the sterilant to the use-dilution concentration. Two endoscopes can be reprocessed and sterilized independently and asynchronously using reprocessing bays 16a, 16b. The endoscopes are mounted on the cassettes 80 and connected to the medical device connector 96 through which the lumen of the endoscope will be pressure washed and sterilized. The reprocessing bay doors 46 are secured and the endoscopes are internally and externally washed with soap and water and rinsed. If necessary, just prior to the sterilization cycle, the endoscopes may be rinsed with hot water to ensure the sterilant will not be cooled upon contact with the endoscopes. The endoscopes are then sterilized internally and externally with sterilant prepared in the reaction chamber 36 just prior to use. The cleaning and sterilization of the endoscope lumen through the medical device connector 96 is assisted by a flow of liquid (soap and water, rinse water, and sterilant in turn). The cleaning phase receives a superimposed pulsating flow of air. This pulsating flow of air causes the liquid flow to become severely unsteady resulting in a scrubbing action on the lumen wall of the endoscope.

During operation of the washing and sterilization cycles, the present invention can detect if the wash bay is in an overflow condition. The reprocessing bays 16a, 16b and the rotating arm members 56a, 56b can be equipped with a speed sensing assembly, generally indicated at 154. The speed sensing assembly includes rotor arm magnets 156 positioned on the rotating arm members 56a, 56b and Hall Effect sensors 158 located in the side walls 48a, 48b. When the reprocessing bays 16a, 16b are in an overflow condition due to an over accumulation of liquid in the reprocessing bay 16a, 16b, the rotational speed of the rotating arm members 56a, 56b will necessarily slow. The Hall Effect sensors 158, which sense the frequency of passage of the rotor arm magnets 156, transmits a frequency signal to the central processor 112 which in turn provides an overflow message to the user interface.

The reprocessing system 10 of the present invention includes a block detection feature which is coordinated and interpreted by the central processor 112. The central processor releases a specific known volume and pressure of air from an air reservoir, preferably a separate 4 liter air reservoir, and the central processor 112 monitors air pressure through the lumen of the endoscope channels by use of a pressure sensor which provides a steady flow of information to the central processor 112. Blockage of channels within the endoscope are determined by changes in pressure or flow rate from established acceptable values and characteristic pressure drop curves. The central processor 112 upon determining a blockage terminates the operation and presents a blockage message to the user interface 152.

The reprocessing system 10 of the present invention includes a leak detection feature that is coordinated and interpreted by the central processor 112. The central processor 112 pressurizes the endoscope jacket with a known air pressure and the central processor 112 monitors the air pressure loss by use of a pressure sensor that provides a steady flow of information to the central processor 112. Leakage is determined by changes in pressure from acceptable values or characteristic pressure drop curves. The central processor 112 upon determining leakage terminates the operation and presents a leakage message to the user interface 152. Air pressure is maintained in the endoscope jacket during reprocessing to protect the endoscope jacket and its contents from exposure to fluids.

A self-cleaning feature of the reprocessing system 10 is accomplished by a self-sterilization cycle controlled by the central processor 112 which controls the pumping of sterilant through tubing lines which can harbor bacteria. The reaction chamber 36 is connected to the water lines which are used for washing the endoscopes as well as rinsing the endoscopes. The flushing of these potential harbors for the growth of bacteria in the self-sterilization cycle maintains the reprocessing system 10 of the present invention in safe working order.

Operation of the reprocessing system 10 is monitored by sensors, including those described above, which provide information to the central processor 112. The central processor 112 receives cycle program instructions from a user including endoscope identification through the user interface 152. The user interface can be equipped with any form of command signal keys or buttons as is well known in the art. Visual displays of user commands which are entered, such as with a touch screen, as well as central processor 112 responses, error messages, status notifications and the like can be presented to the user at the user interface 152. A printer capability can be included to permit the central processor 112 to provide written records of any aspect of reprocessing system operation to the user. Printed records of specific endoscope sterilization can also be printed at the completion of a reprocessing and sterilization cycle. All aspects of the operation of the reprocessing system 10 can be controlled by the central processor 112, to include measuring and mixing of chemical components for the sterilant, metering of water to the reaction chamber 36 for sterilant dilution purposes, washing, rinsing and sterilizing cycles, self-sterilizing, blockage detection and user notification, door ajar sensing and responsive operation termination, and other similar system monitoring and operational controls.

Figure 9:
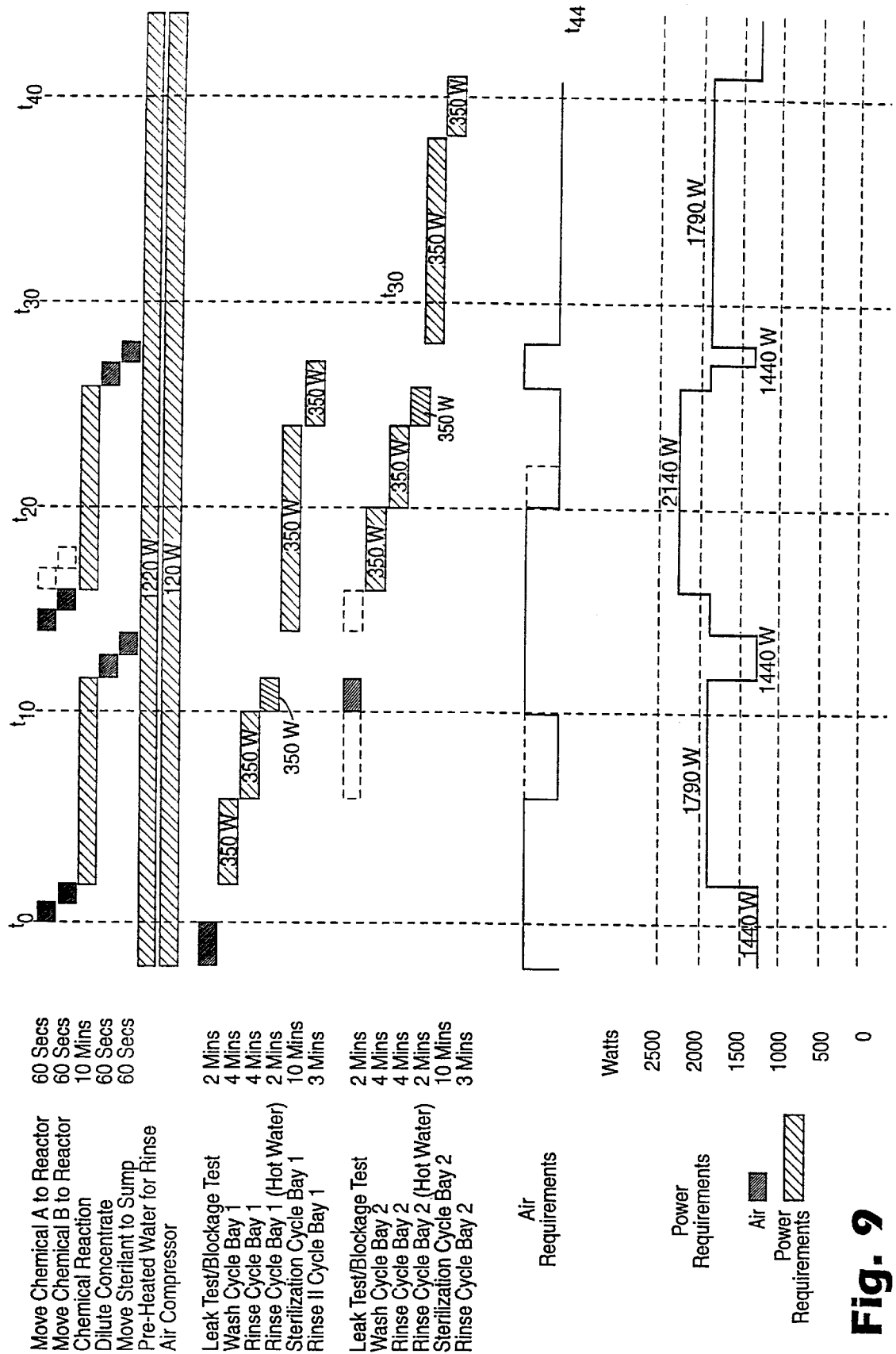
FIG. 9 is a bar graph representation of the cycle time, air and electrical power requirements of a medical instrument reprocessing device according to the principles of the present invention.
Figure 10A:
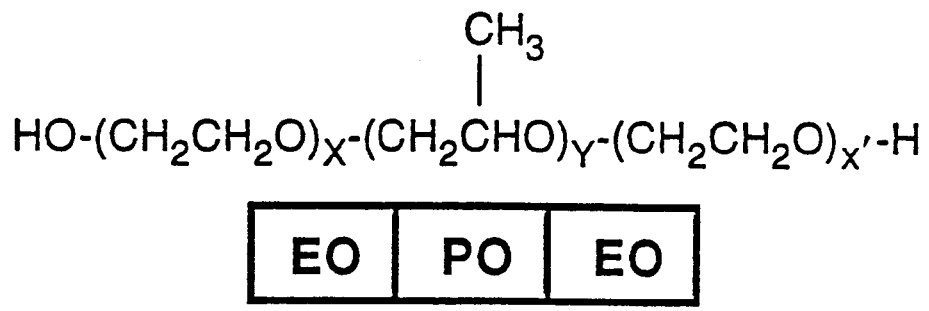
FIGS. 10A–10D show the chemical structures of PLURONIC (L-44), PLURONIC-R, TETRONIC, and TETRONIC-R surfactants, respectively, which are suitable for use in a sterilant which can be used in combination with the reprocessing device according to the principles of the present invention.
Figure 10B:
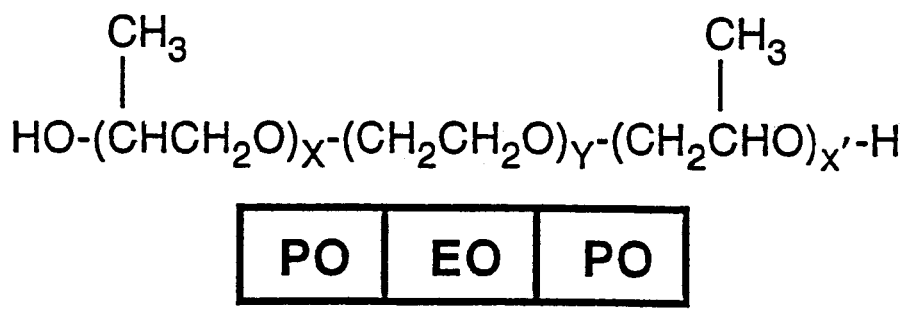
Figure 10C:
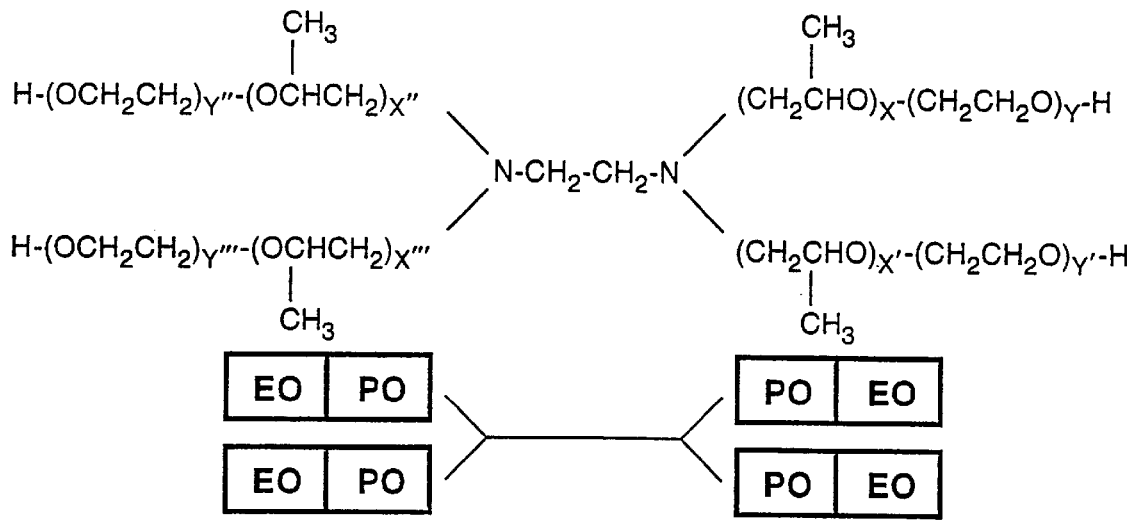
Figure 10D:
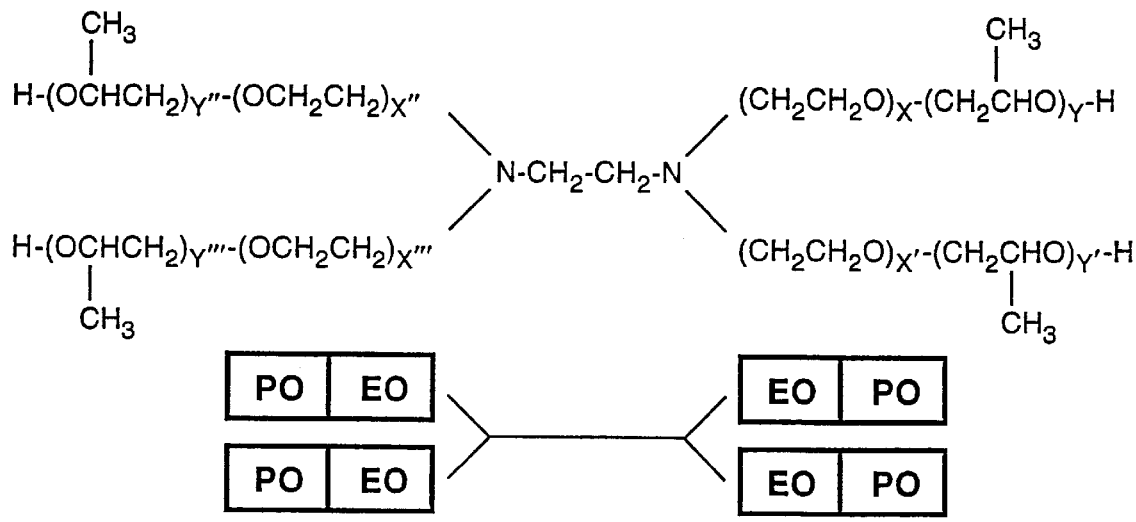

The electrical requirements for the reprocessing system 10 are provided so as to ensure a constant RPM for the electric motors and pumps 40, regardless of the input line frequency (50 or 60 HZ). AC motor speed is influenced by the input line frequency. In the present invention, using a solid state inverter circuit, which is commercially available, the single phase input power is converted to 3-phase power for the electric motor 40. The inverter converts the input AC power to DC and then reconverts the DC power to 3-phase AC power. This power supply process provides for electric motor and pump 40 operation which is insensitive to the input line frequency. FIG. 9 provides a bar graph representation of cycle time, air and electrical power requirements for the preferred embodiment of the reprocessing system 10 of the present invention.

Sterilant:

The concept of the present invention includes the use of the device described above in combination with an anti-microbial, sterilization solution that is capable of sterilizing objects containing microbes, such as bacterial endospores, at room temperature, yet exhibits superior anti-corrosive properties.

In accordance with a further aspect of this invention, the reprocessing device 10 described above is preferably used in combination with a multi-component concentrate system comprising at least two components or parts capable of being mixed and diluted with water into a sterilization solution exhibiting superior anti-corrosive properties. In one embodiment, the first component comprises hydrogen peroxide and water, whereas the second component comprises formic acid and water.

The concentrate system further includes at least one surfactant, phosphoric acid, and at least one corrosive inhibitor. Preferably, the corrosive inhibitor(s) is/are contained in the first component and the surfactant(s) and phosphoric acid are contained in the second component.

Mixing of the first and second components causes the formic acid to react with the hydrogen peroxide to form performic acid. Preferably, the two-part or multi-part concentrate system is substantially free of any alcohol that is reactable with the formic acid to form an ester, e.g., ethyl formate, methyl formate, propyl formate to keep formic acid available for reaction. It is also preferred that the two-part or multi-part concentrate system be devoid of a sulfur-containing catalyst.

The surfactant incorporated into the two-component concentrate system should have a synergistic effect of making the resulting sterilization solution more efficacious and more rapid with respect to its germicidal effect. The surfactant used could be any of a class of zwitterionic, amphoteric, anionic, nonionic or cationic, and should be soluble in either of two concentrate components, preferably formic acid, and should be low foaming as to require fewer rinse cycles. Preferred for the purposes of this invention are PLURONIC (L-44), PLURONIC-R, TETRONIC, and TETRONIC-R surfactants, the chemical structures for these block copolymer surfactants are shown in FIGS. 5–8, respectively. These surfactants are available from BASF of Parsippany, N.J. These surfactants disrupt the microbes' surface membranes making them more porous and permeable and allowing the chemical microbicide to enter. The surfactant may be incorporated into the first component and/or the second component, or added separately as a third component; however it is preferable to incorporate the surfactant in the component containing formic acid to eliminate the formation of oxidative by-products produced by the hydrogen peroxide reacting with the surfactant upon storage and to insure a homogenous solution.

The corrosion inhibitor is preferably 1,2,3-benzotriazole (C-99), supplied by PMC Specialties Group, Inc. The corrosion inhibitor may also be incorporated into the first component and/or the second component, or added separately as a third component; however, it is preferable to incorporate the corrosion inhibitor in the component containing hydrogen peroxide because of enhanced chemical stability in a non-acidic environment.

In a preferred embodiment, the multi-part concentrate system is a two-component system, with the first component comprising about 30 wt % to about 50 wt % of hydrogen peroxide, and about 1.8 wt % to about 10 wt % of benzotriazole and the remainder water; and the second component comprising about 20 wt % to about 95 wt % of formic acid, about 2.5 wt % to about 12 wt % of block copolymer, and about 4 wt % to about 20 wt % of phosphoric acid and the remainder water.

More preferably, the two-component system comprises about 40 wt % to about 50 wt % of hydrogen peroxide, and about 1.8 wt % to about 2.3 wt % of benzotriazole and the remainder water; and the second component comprises about 20 wt % to about 30 wt % of formic acid, about 2.5 wt % to about 4 wt % of block copolymer, and about 4 wt % to about 6 wt % of phosphoric acid and the remainder water.

Still even more preferably, the first component comprises about 50 wt % of the hydrogen peroxide, about 2.3 wt % of benzotriazole, and the remainder water, while the second component comprises about 25 wt % of formic acid, about 3.3 wt % of block copolymer, and about 5.0 wt % of phosphoric acid, and the remainder water. In this embodiment, the ratio of the first component to the second component is preferably about 60:40.

The first and second components (and any additional components) of the concentrate system may be packaged physically separate from each other and mixed before use.

To form an activated solution, the first and second components are mixed together, preferably in a ratio of about 60:40. The resulting activated solution is preferably about 10 wt % formic acid, about 1.38 to 1.4 wt % block copolymer (L-44), about 0.1–2.0 wt % phosphoric acid, about 30 wt % $H_2O_2$, about 1.38 to 1.4 wt % benzotriazole (C-99) and the remainder water. More preferably, the initial activated solution contains 1.38 wt % C-99 and 1.38 wt % L-44. Within minutes at 45°–55° C. and within hours at room temperature, the activated solution reaches equilibrium wherein the composition contains: about 25 wt % hydrogen peroxide, about 6.5 wt % formic acid, about 4.5 to 5.0 wt % performic acid, 1.38 wt % C-99, 1.38 wt % L-44 and 2.0 wt % $H_2PO_4$, and the remainder water. The weight percentages of C-99, L-44 and $H_2PO_4$ do not change from time zero to equilibrium. The $H_2O_2$ to formic/performic acid ratio is preferably 1:0.33.

The two-part or multi-part concentrate system is mixed to form the activated solution and is allowed to react for approximately 0.5–30 minutes. The speed of reaction time in forming the activated solution is critically important for market acceptance of the product. The reaction time of the present invention is an advantageously short reaction time. The activated solution can preferably be mixed in a machine because of its low foaming quality but also can be mixed manually. The mixing and reaction time for component A and B is 30–60 minutes at room temperature and 5–10 minutes at 45–55° C. before the activated solution is ready for further dilution and use.

The activated solution may be used for as long as 48 hours after activation before the performic acid in the solution diminishes, affecting ultimate efficacy. Therefore, the components A and B are generally packaged and stored as two-separate packaging system components and are preferably mixed at a user's facility shortly before actual use.

If much less than about 25 wt % of formic acid is used in the concentrate system, the reaction to form the activated solution will not proceed quickly enough. It is important that the reaction proceed quickly in order to generate on demand the active anti-microbial component at effective concentrations.

To make a use-dilution solution, the activated solution is diluted to a ratio of from 2–17 wt % of activated solution to from 98–83 wt % of water. The use-dilution solution achieves a 100% kill of bacterial spores at 40°–50° C. in 15 minutes or less. The above ratio of hydrogen peroxide to formic/performic acid in the active solution is most effective in achieving a 100% kill of bacterial spores in 20 minutes or less.

The use-dilution solution comprises:
about 0.05 wt % to about 0.5 wt % performic acid, more preferably about 0.1 wt % to 0.5 wt % and most preferably 0.3 wt %;
about 0.4 wt % to about 6.0 wt % hydrogen peroxide, more preferably about 3.0 wt % to about 6.0 wt % and most preferably about 5.0 wt % to about 5.5 wt %;
about 0.07 wt % to about 1.5 wt % formic acid, and most preferably about 0.05 wt % to 1.5 wt %;
preferably about 0.1 wt % to about 1.0 wt % benzotriazole, and most preferably 0.2 wt %;
preferably about 0.1 wt % to about 0.5 wt % and more preferably 0.2 wt % block copolymer of ethylene oxide and propylene oxide (also referred to herein as a polyoxypropylene-polyoxyethylene block copolymer);
preferably about 0.1 wt % to about 0.5 wt % phosphoric acid, and most preferably 0.3 wt %;
and the remainder water.

Purified water is not required for diluting the activated solution to achieve the use-dilution solution. Commercially, this is a significant advantage, because tap water is more readily available and is less expensive to provide than purified or deionized water and more convenient for the end user.

The synergistic effect among the ethylene oxide/ propylene oxide block-copolymer, the benzotriazole, and phosphoric acid (collectively referred to herein as the anti-corrosive system) surprisingly reduces corrosion by a factor of 10 over simply one or two of the elements alone. As mentioned above, the multi-part concentrate system is operative without the intervention of and is preferably substantially free of sulfur-containing catalysts, such as sulfuric and sulfonic acid catalysts, that interfere with the anti-corrosive properties exhibited by the synergism of the anti-corrosive system.

The two-part concentrate system, activated solution and use-dilution solution are all biodegradable. The concentrations selected for the activated solution are cost effective because they minimize the amount of aqueous solution needed, and reduce the time necessary to form the active ingredients (i.e. $H_2O_2$ and PFA)in the temperature range of 20–55° C. to become an effective sporicidal agent.

The two-part concentrate system can be stored for up to one year. After mixing the first and second components together, the activated solution must be further diluted to form the use-dilution solution. The use-dilution solution must be used within 48 hours because performic acid will degrade in the activated solution to a point where a use-dilution formulation will no longer be efficacious, i.e. kill spores within the desired amount of time.

To sterilize instruments, substrates, surfaces, etc., the use-dilution solution is applied to the object to be sterilized. Preferably, the use-dilution solution is applied within 1 hour of preparation at room temperature. Depending on the surface composition of the substrate (e.g. porous vs. non-porous, smooth vs. creviced) the use-dilution solution kills 100% of spores in 1–30 minutes at room temperature (20–25° C.). At elevated temperatures (40–50° C.) the use-dilution solution achieves 100% kill in 1–30 minutes and in as little as from 1–5 minutes, depending on the surface composition of the substrate. The period of time that the instruments are exposed to the use-dilution solution should be set to a period in which 100% of all microorganisms are killed. The composition of the invention is also useful at a temperature range of 20–50° C.

The instruments are then rinsed with sterile water until free of the sterilizing solution and are then sterile and ready for reuse or for storage in sterile packaging.

The present invention provides an improved device and an improved fast acting, low-corrosivity, sterilant which can be used in combination to reprocess and sterilize sensitive medical instruments with lumens, such as endoscopes.

The foregoing detailed description of the preferred embodiments of the invention has been provided for the purposes of illustration and description. It is not intended to be exhaustive or to limit the invention to the precise embodiments disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus for sterilizing an endoscope, said apparatus comprising:
    (a) at least one reprocessing bay, each said bay comprising:
        (i) walls and a door together defining an interior reprocessing chamber, said door providing selective access to said reprocessing chamber;
        (ii) a fluid inlet defined in one of said walls;
        (iii) a fluid outlet defined in one of said walls, said fluid outlet permitting removal of accumulated fluid in said reprocessing bay;
        (iv) a rotating arm unit rotatably mounted to one of said walls so as to be disposed within said reprocessing chamber, said rotating arm unit including at least one rotating arm member having an interior fluid passage fluidly connected to said fluid inlet, a plurality of orifices being defined in said rotating arm member, said orifices being in fluid communication with said fluid passage, so that fluid can pass from said fluid inlet, through said fluid passage, through said orifices and into said reprocessing chamber;
    (b) a reaction vessel;
    (c) at least one sterilant conduit extending between and fluidly coupling said reaction vessel and said reprocessing chamber;
    (d) at least one chemical sterilant component container;
    (e) a chemical sterilant component conduit extending between and fluidly coupling each said chemical sterilant component container to said reaction vessel;
    (f) at least one water conduit fluidly coupling a water supply to at least one of said reprocessing chamber, said reaction vessel, and the conduits extending therebetween; and
    (g) a transfer control system for selectively transferring at least one chemical sterilant component from said at least one chemical sterilant component container to said reaction vessel, for selectively transferring sterilant from said reaction vessel to said reprocessing chamber, and for selectively transferring water from a water supply through said at least one water conduit.

2. An apparatus according to claim 1, further comprising: a heater for controlling a temperature of said sterilant.

3. An apparatus according to claim 1, comprising at least two reprocessing bays.

4. An apparatus according to claim 3, wherein the transfer control system includes two pumps, one for each reprocessing bay, each fluidly connected to said reaction vessel for moving fluid from said reaction vessel through respective sterilant conduits to the fluid inlet of the respective reprocessing bay.

5. An apparatus according to claim 4, wherein said transfer system further comprises a central processor, said central processor being operatively connected to said pumps, said central processor having sufficient processing capability to selectively asynchronously operate said pumps.

6. An apparatus according to claim 5, further comprising a user interface, said user interface being operationally connected to said central processor.

7. An apparatus according to claim 1, in combination with at least one endoscope having a lumen which terminates at one end with a first connector, and wherein said apparatus further comprises a second connector, complementary to said first connector, said second connector being in fluid communication with said at least one sterilant conduit.

8. An apparatus according to claim 1, further comprising a chemical concentration detector, said chemical concentration detector being located within said reaction vessel and operatively connected to said central processor.

9. An apparatus according to claim 1, wherein the transfer control system includes an air compressor, said air compressor being pneumatically connected to said chemical sterilant component container, wherein said air compressor has a capacity to provide sufficient air pressure to said chemical sterilant component container to selectively effect transfer of a chemical sterilant component from said chemical sterilant component container to said reaction vessel.

10. An apparatus according to claim 1, further comprising a load sensor, said load sensor being connected to said reaction vessel being operatively connected to said central processor for sensing and indicating an amount of material in said reaction vessel.

11. An apparatus according to claim 1, further comprising at least one cassette movably mounted within said reprocessing chamber.

12. An apparatus according to claim 11, wherein said cassette is configured to removably hold an endoscope within said reprocessing chamber.

13. An apparatus according to claim 1, wherein said at least one chemical sterilant component container comprises a first component container and a second component container.

14. The apparatus of claim 13 in combination with a sterilant, said sterilant comprising:
an anti-microbial two-part concentrate system comprising:
  a first component comprising hydrogen peroxide and water;
  a second component comprising formic acid and water;
  a block copolymer of ethylene oxide and propylene oxide, said block copolymer being present in said first component, said second component, or said first and second components;
  phosphoric acid present in said first component, said second component, or said first and second components; and
  benzotriazole present in said first component, said second component, or said first and second components,
wherein, prior to mixture to form said sterilant, said first component and said second component are respectively contained in said first component container and said second component container.

15. The combination according to claim 14, wherein said two-part concentrate system is substantially free of an alcohol reactable with said formic acid to form an ester.

16. The combination according to claim 14, wherein said two-part concentrate system is devoid of a sulfur-containing catalyst.

17. The combination according to claim 14, wherein a ratio of said first component to said second component is 60:40.

18. The combination according to claim 14, wherein said second component contains said block copolymer and said phosphoric acid and, and further wherein said first component contains said benzotriazole.

19. The combination according to claim 18, wherein in the two-part concentrate system:
said second component comprises about 25 wt % to about 95 wt % of said formic acid, about 3 wt % to about 12 wt % of said block copolymer, and about 4 wt % to about 20 wt % of said phosphoric acid, and
said first component comprises about 30 wt % to about 50 wt % of said hydrogen peroxide, and about 2 wt % to about 10 wt % of said benzotriazole.

20. The combination according to claim 19, wherein in the two-part concentrate system:
said second component comprises about 25 wt % of said formic acid, about 3.3 wt % of said block copolymer, and about 5 wt % of said phosphoric acid, and the remainder water; and said first component comprises about 50 wt % of said hydrogen peroxide, about 2.3 wt % of said benzotriazole, and the remainder water.

21. An apparatus according to claim 1, wherein said reprocessing bay is vertically oriented, said vertical orientation keeping said endoscope in a suspended position above said accumulated fluid in said reprocessing bay.

22. A method of sterilizing an endoscope, said method comprising:
(I) providing an apparatus, said apparatus comprising:
  (a) at least one reprocessing bay, each said bay comprising:
    (i) walls and a door together defining an interior reprocessing chamber, said door providing selective access to said reprocessing chamber;
    (ii) a fluid inlet defined in one of said walls;
    (iii) a fluid outlet defined in one of said walls;
    (iv) a rotating arm unit rotatably mounted to one of said walls so as to be disposed within said reprocessing chamber, said rotating arm unit including at least one rotating arm member having an interior fluid passage fluidly connected to said fluid inlet, a plurality of orifices being defined in said rotating arm member, said orifices being in fluid communication with said fluid passage, so that fluid can pass from said fluid inlet, through said fluid passage, through said orifices and into said reprocessing chamber;
  (b) a reaction vessel;
  (c) at least one sterilant conduit extending between and fluidly coupling said reaction vessel and said reprocessing chamber;
  (d) at least one chemical sterilant component container;
  (e) a chemical sterilant component conduit extending between and fluidly coupling each said chemical sterilant component container to said reaction vessel;
  (f) at least one water conduit fluidly coupling a water supply to at least one of said reprocessing chamber, said reaction vessel, and the conduits extending therebetween; and
  (g) a transfer control system for selectively transferring at least one chemical sterilant component from said at least one chemical sterilant component container to said reaction vessel, for selectively transferring said sterilant from said reaction vessel to said reprocessing chamber, and for selectively transferring water from a water supply through said at least one water conduit;
(II) disposing an endoscope to be sterilized in a said reprocessing bay;
(III) transferring at least one chemical sterilant component from said chemical sterilant component container to said reaction vessel;
(IV) preparing a sterilant in said reaction vessel;
(V) transferring said sterilant from said reaction chamber to a said reprocessing bay; and
(VI) forcing said sterilant under pressure through said fluid passage of said rotating arm member and through said plurality of orifices into a said bay to effectively sterilize said endoscope.

23. The method of claim 22, wherein said apparatus comprises at least two bays, said bays being operated asynchronously with overlapping operating time cycles.

24. The method of claim 22, further comprising at least two chemical sterilant component containers, each of said containers containing one part of a two-part chemical sterilant concentrate system to be prepared in said reaction vessel.

25. The method of claim 24, wherein said one part of a two-part chemical sterilant concentrate system in each of said chemical component containers is transferred from said chemical component container to said reaction vessel by pneumatic force.

26. The method of claim 25, wherein said pneumatic force is provided by an air compressor.

27. The method of claim 22, after disposing an endoscope to be sterilized in a said reprocessing bay and before transferring said sterilant from said reaction chamber to a said reprocessing bay, further comprising:

cleaning said endoscope with soap, and rinsing said endoscope with water.

28. The method of claim 22, after preparing a sterilant in said reaction vessel and before transferring said sterilant from said reaction chamber to said reprocessing bay, further comprising maintaining the temperature of said sterilant from about 20° C. to about 55° C.

29. The method of claim 22, wherein the apparatus further comprises a load sensor, said load sensor being connected to said reaction vessel for sensing load data from said reaction vessel, and a central processor operationally connected to said load sensor and wherein transferring at least one chemical sterilant component from said chemical sterilant component container to said reaction vessel comprises the transfer of one chemical component and wherein sensing the load data of the reaction vessel and transmitting said load data from said load sensor to said central processor occurs after said transferring at least one chemical sterilant component from said chemical sterilant component container to said reaction vessel, said transferring and said sensing being repeated in order at least once.

30. The method of claim 29, after the at least once repeated transferring and sensing further comprising:

calculating a dilution measurement amount of water in the central processor; and transferring said dilution measurement amount of water to said reaction vessel.

31. The method of claim 29, wherein said central processor is programmable to effect an apparatus self-sterilization cycle after completion of endoscope sterilization.

32. The method of claim 22, after forcing said sterilant under pressure further comprising:

self-sterilizing said apparatus.

* * * * *